US008796417B2

(12) United States Patent
Shiba et al.

(10) Patent No.: US 8,796,417 B2

(45) Date of Patent: Aug. 5, 2014

(54) THREE-DIMENSIONAL STRUCTURE OF FUNCTIONAL MATERIAL

(75) Inventors: Kiyotaka Shiba, Kawasaki (JP); Kenichi Sano, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 1542 days.

(21) Appl. No.: 11/915,480

(22) PCT Filed: May 24, 2006

(86) PCT No.: PCT/JP2006/310367

§ 371 (c)(1), (2), (4) Date: Sep. 3, 2009

(87) PCT Pub. No.: WO2006/126595

PCT Pub. Date: Nov. 30, 2006

(65) Prior Publication Data

US 2010/0040862 A1 Feb. 18, 2010

(30) Foreign Application Priority Data

May 27, 2005 (JP) ................................. 2005-155438

(51) Int. Cl.

| | |
|---|---|
| ***C07K 7/06*** | (2006.01) |
| ***B32B 5/16*** | (2006.01) |
| ***C23C 28/04*** | (2006.01) |
| ***C07K 14/79*** | (2006.01) |
| ***C07K 7/08*** | (2006.01) |
| ***B82Y 30/00*** | (2011.01) |
| ***C23C 26/00*** | (2006.01) |

(52) U.S. Cl.

CPC ............... *C23C 26/00* (2013.01); *C23C 28/042* (2013.01); *C23C 28/048* (2013.01); *C07K 7/06* (2013.01); *C07K 14/79* (2013.01); *C07K 7/08* (2013.01); *B82Y 30/00* (2013.01)

USPC ............................ 530/329; 427/414; 530/400

(58) Field of Classification Search

None

See application file for complete search history.

(56) References Cited

U.S. PATENT DOCUMENTS

| | | | | |
|---|---|---|---|---|
| 7,498,403 | B2 * | 3/2009 | Shiba et al. | 530/327 |
| 2003/0113714 | A1 * | 6/2003 | Belcher et al. | 435/5 |
| 2005/0170336 | A1 * | 8/2005 | Belcher et al. | 435/5 |
| 2007/0112174 | A1 * | 5/2007 | Shiba et al. | 530/329 |

FOREIGN PATENT DOCUMENTS

| | | | |
|---|---|---|---|
| JP | 2001-191446 | | 7/2001 |
| WO | WO 2005010031 | * | 2/2005 |

OTHER PUBLICATIONS

Tamerler et al ('Biomimetic multifunctional molecular coatings using engineered proteins' Progress in Organic Coatings 47 (2003) pp. 267-274).*

Basics of Semiconductors, from http://enpub.fulton.asu.edu/widebandgap/NewPages/SCbasics.html, pp. 1-4, accessed Aug. 22, 2013.*

Sano et al., "Endowing a Ferritin-Like Cage Protein with High Affinity and Selectivity for Certain Inorganic Materials," SMALL, vol. 1, No. 8-9, pp. 826-832, Aug. 2005.

Sano et al., "Utilization of the Pleiotropy of a Peptidic Aptamer to Fabricate Heterogeneous Nanodot-Containing Multilayer Nanostructures," Journal of American Chemical Society, vol. 128, No. 5, pp. 1717-1722, Jan. 18, 2006.

Supplementary European Search Report from corresponding EP 06746798.5 dated Jan. 23, 2009.

Sano et al., "Specificity and Biomineralization Activities of Ti-Binding Pepetide-1 (TBP-1)," Langmuir, 21:7, 3090-3095, Mar. 29, 2005.

Sano et al., "A Hexapeptide Motif that Electrostatically Binds to the Surface of Titanium," J. Am. Chem. Soc., 125:47, 14234-14235, 2003.

Brott et al., "Ultrafast Holographic Nanopatterning of Biocatalytically formed Silica," Nature, 413:6863, 291-293, Sep. 20, 2001.

He et al., "Nucleation of Apatite Crystals in vitro by Self-Assembled Dentin Matrix Protein 1," Nature Materials, 2:8, 552-558, Aug. 2003.

* cited by examiner

*Primary Examiner* — Julie Ha

*Assistant Examiner* — Li Ni Komatsu

(74) *Attorney, Agent, or Firm* — Kenneth H. Sonnenfeld; Margaret B. Brivanlou; King & Spalding LLP

(57) ABSTRACT

It is to provide an inorganic thin film of titanium dioxide or the like which is controlled at the nanoscale and a three-dimensional structure of a functional material such as semiconductor nanoparticles. A three-dimensional structure of an inorganic material is manufactured by introducing onto a surface of an inorganic substrate ferritin presenting on its surface a plurality of inorganic material-binding peptides; binding the ferritin in a monolayer onto the inorganic substrate; introducing an inorganic material onto the ferritin which is bound in a monolayer, while the inorganic material-binding peptides is having a binding and/or biomineralization ability for the inorganic material; forming a biomineral layer utilizing the biomineralization ability of the inorganic material-binding peptides; and subsequently repeating one or more times the steps (a) and (b) of a multilayering operation: (a) introducing onto the biomineral layer thus formed the ferritin having a binding ability to the biomineral layer, and binding the ferritin in a monolayer onto the biomineral layer; (b) introducing the inorganic material onto the surface of the ferritin which is bound in a monolayer, and forming a biomineral layer.

3 Claims, 11 Drawing Sheets

A. Mirror-polished titanium substrate

B. The first Fe-minT1-LF layer

C. The first silica layer

D. The second Fe-minT1-LF layer

E. The second silica layer

THREE-DIMENSIONAL STRUCTURE OF FUNCTIONAL MATERIAL

TECHNICAL FIELD

The present invention relates to a monolayer thin film of an inorganic material and a manufacturing method thereof; and a three-dimensional structure of a functional material and a manufacturing method thereof, by utilizing a biomineralization ability of an inorganic material-binding peptide.

BACKGROUND ART

As for an artificial peptide which specifically binds to an inorganic material, it was reported that an iron oxide ($Fe_2O_3$)-binding peptide was obtained by S. Brown in 1992 (for example, see non-patent document 1). Since then, artificial peptides which bind to an inorganic material that had not been utilized by living organisms in nature until then have been obtained successively. In 2000, A. M. Belcher reported an artificial peptide binding to gallium arsenide (GaAs) (for example, see non-patent document 2) and an artificial peptide binding to calcium carbonate ($CaCO_3$) (for example, seen on-patent document 2). Further, although a detailed mechanism of the reaction remains unknown, it is known that an inorganic material-binding peptide has a biomineralization ability for its target material.

Meanwhile, inorganic material-binding peptide motifs that have been found from inorganic materials utilized by living organisms in nature, for example, such as a silicon skeleton of diatom, a shell composed of calcium carbonate, human tooth or bone, are known to have a biomineralization ability for their target materials just like artificial peptides. Peptides that bind to an inorganic material are generally considered to be multifunctional peptides having a binding ability to a target material and biomineralization ability for the target material at the same time.

The present inventors have isolated by a phage display method, the artificial peptide TBP-1 (RKLPDAPGMHTW; SEQ ID NO: 2) that binds to titanium (for example, see non-patent document 3). TBP-1 has an ability to bind to silver and silicon other than titanium, but does not bind to gold, platinum, copper, chromium, iron, tin, or zinc, showing a high binding specificity. Further, TBP-1 has an ability to biomineralize silver or silica, and thus is also shown to be a multifunctional peptide (for example, see non-patent document 4).

Efforts have been made towards establishing a technology for controlling the positioning of functional particles at the nanoscale by utilizing these inorganic material-binding peptides. Researches have been made mainly on the following two methods. The first one is a method utilizing the binding specificity of an inorganic material-binding peptide, which is called "a direct patterning", comprising the steps of modifying a substrate with plural kinds of inorganic materials, and positioning functional particles of interest two-dimensionally just on the specific region modified with an inorganic material. The second one is a method comprising the steps of patterning inorganic material-binding peptides by coupling such inorganic material-binding peptides on a molecular scaffold having a periodic structure or an orderly structure; and causing a "biomineralization" reaction of functional molecules on this scaffold, thereby controlling the positioning of the functional molecules. Both of these methods have been actively studied.

On the other hand, ferritin proteins have been known for long years as a protein which stores 'atoms of "iron", which is an essential metal and is toxic at the same time' in living bodies. Ferritin or Ferritin-like proteins exist universally, in a wide range of organisms from animals and plants to bacteria, and is deeply related to the homeostasis of iron element in living bodies or in cells. Ferritin from higher eucaryotes such as human and horse forms a spherical shell structure consisting of a 24-mer, approximately 12 nm in diameter, formed from peptide chains whose molecular weight is about 20 kDa, and has an interior space of 7 to 8 nm. Ferritin stores an iron molecule in this interior space as a mass of nanoparticulate iron oxide. With regard to 24 subunits which constitute a protein spherical shell (cage), there are two types (type H and type L), and the constitution ratio of these types varies depending on organism species and tissues.

Ferritin stores an iron nanoparticle inside it under natural circumstances. However, under artificial circumstances, it has been revealed that ferritin can store the following substances in addition to iron: oxides of beryllium, gallium, manganese, phosphorus, uranium, lead, cobalt, nickel, chromium and the like; and nanoparticles of semiconductors and magnets such as cadmium selenide, zinc sulfide, iron sulfide and cadmium sulfide. Consequently, applied researches of ferritin in the fields of semiconductor-material engineering and of socialized health care have been actively performed.

Further, it is known that a dendrimer is a three-dimensional giant molecule synthesized step-by-step from a single branched-monomer unit and that the characteristic and functionality of a dendrimer can be controlled and modified easily. A dendrimer is synthesized by repeatedly adding building blocks (basic units) in the direction away from a multifunctional core (a divergence-type approach to synthesis) or in the direction towards a multifunctional core (convergence-type approach to synthesis), and on each occasion that a three-dimensional shell of building blocks is added, a dendrimer of a higher-generation is formed. It is also known that the density of functional groups on the surface increases as the dendrimer generation advances, which causes the dendrimer to have a greater control over the physical property. For example, integrating a hydrophilic group such as a carboxyl group into terminal functional groups makes the dendrimer soluble. It is also possible to design a dendrimer whose inside is hydrophobic while the molecular surface is hydrophilic. A dendrimer has a three-dimensional structure and provides a space inside for keeping a guest molecule, which allows a dendrimer to uptake poor water-soluble drugs. Further, it is known that a PAMAM (poly(amideamine)) dendrimer whose terminal functional groups are amino groups, is protonated at the terminal amino groups in response to an external environment such as pHs, which causes the whole dendrimer molecule to become positively charged and become larger in volume.

Furthermore, a star polymer is generally defined as a polymer having three or more polymer chains to be arms, which are connected at the core, the center of the arms. As the center core, a polyfunctional polyhalogenated compound or a cross-linked polymer of polyfunctional monomers is used. In addition, a star polymer with ten or more arms (a multi-arm star polymer) is produced by a method comprising the step of cross-linking polymer chains of monocarbanion with divinylbenzene by using a cross-linked structure of divinylbenzene as a core. Common methods for producing a starpolymer are a manufacturing method comprising coupling anionic living polymers by a polyfunctional coupling agent (an arm-first method); and a method comprising synthesizing a polyfunctional initiating seed in advance and extending the arms therefrom (a core-first method). A polymerization reaction of polymer chains to be arms, and a reaction to couple a plurality of such polymer chains to the core that is supposed to be the center, are performed separately in two stages.

Patent Document 1: Japanese Laid-Open Patent Application No. 2003-282509

Patent Document 2: Japanese Laid-Open Patent Application No. 2004-374093

Non-Patent Document 1: Proc. Natl. Acad. Sci. USA 89: 8651-, 1992

Non-Patent Document 2: Nature, 405: 665-, 2000

Non-Patent Document 3: Sano K., and ShibaK. "Δhexapeptide motif that electrostatically binds to the surface of titanium" J Am Chem Soc. 125, 14234-5 (2003)

Non-Patent Document 4: Langmuir, 21 (7), 3090-3095, 2005

DISCLOSURE OF THE INVENTION

Object to be Solved by the Invention

Biotechnology and nanotechnology, that are attracting the greatest attention in cutting-edge technology fields, are closely related to each other. Bio-nanotechnology is the fusion of these two technologies and is attracting attention as a new fundamental technology which is indispensable for the society of 21st century. When considering the application and utilization of the bio-nanotechnology in various fields, a technique of a three-dimensional positioning of molecules utilizing a bottom-up type self-assembly becomes necessary. The object of the present invention is to provide a three-dimensional structure of a functional material, in which a bottom-up type three-dimensional positioning of molecules at the nanoscale has been enabled with regard to a protein, virus, block copolymer and the like, to which an inorganic material-binding peptide is bound/fused; and a thin film controlled at the nanoscale by controlling the positioning of molecules in the thickness direction, by utilizing multifuctionality of an inorganic material-binding peptide, that is, both an ability to specifically bind to a particular inorganic material and a biomineralization ability.

Means to Solve the Object

The present inventors have made a keen study for solving the above-mentioned object, and have found that a monolayer thin film of an inorganic material and a three-dimensional structure of a functional material can be produced by the following steps: fusing cDNA encoding the amino-terminal of horse spleen-derived type L ferritin molecule with DNA encoding an inorganic material-binding peptide consisting of the amino acid sequence of RKLPDA shown by SEQ ID NO: 1; expressing a ferritin protein fused with an inorganic material-binding peptide by utilizing *Escherichia coli*; purifying the fused ferritin protein; and utilizing a biomineralization ability of the inorganic material-binding peptide of the fused ferritin protein, with the use of the obtained fused ferritin protein as a model system. This led to the completion of the present invention.

More specifically, the present invention relates to a method for manufacturing a monolayer thin film of an inorganic material, comprising the steps of introducing onto a surface of an inorganic substrate an aggregate presenting on its surface a plurality of the same or different inorganic material-binding peptides; binding the aggregate in a monolayer onto the inorganic substrate; introducing onto the aggregate which is bound in a monolayer, a substrate or a precursor for a biomineralization reaction of the inorganic material-binding peptides; and forming a biomineral layer by utilizing a biomineralization ability of the inorganic material-binding peptides ("1")

The present invention also relates to a monolayer thin film of an inorganic material, wherein, via an aggregate which is bound in a monolayer onto a surface of an inorganic substrate and is presenting on its surface a plurality of the same or different inorganic material-binding peptides, a substrate or a precursor for a biomineralization reaction of the inorganic material-binding peptides is formed as a biomineral layer by a biomineralization ability of the inorganic material-binding peptides ("2"); the monolayer thin film of an inorganic material according to "2", wherein the inorganic material-binding peptide is RKLPDA (SEQ ID NO:1) or RKLPDAPGMHTW (SEQ ID NO:2) ("3"); the monolayer thin film of an inorganic material according to "2", wherein the inorganic material-binding peptide is a peptide consisting of an amino acid sequence that exists in nature ("4"); the monolayer thin film of an inorganic material according to any one of "2" to "4", wherein the aggregate is a fusion protein complex in which a plurality of the same or different inorganic material-binding peptides are fused ("5"); the monolayer thin film of an inorganic material according to "5", wherein the fusion protein complex is a ferritin protein complex derived from a higher eucaryote ("6"); of an inorganic substrate an aggregate presenting on its surface a plurality of the same or different inorganic material-binding peptides; binding the aggregate in a monolayer onto the inorganic substrate; introducing onto the aggregate which is bound in a monolayer, a substrate or a precursor for a biomineralization reaction of the inorganic material-binding peptides; forming a biomineral layer utilizing the biomineralization ability of the inorganic material-binding peptides; and subsequently repeating one or more times the steps (a) and (b) of a multilayering operation: (a) introducing onto a surface of the biomineral layer thus formed the aggregate having a binding ability to the biomineral layer, and binding the aggregate in a monolayer onto the biomineral layer by utilizing the binding ability of the inorganic material-binding peptides to the biomineral layer; (b) introducing onto a surface of the aggregate which is bound in a monolayer, a substrate or a precursor for a biomineralization reaction of the inorganic material-binding peptides, and forming a biomineral layer by utilizing the biomineralization ability of the inorganic material-binding peptides ("9"); and a method for manufacturing a three-dimensional structure of a functional material, comprising the steps of introducing onto a surface of an inorganic substrate an aggregate presenting on its surface a plurality of the same or different inorganic material-binding peptides; binding the aggregate in a monolayer onto the inorganic substrate; introducing onto the aggregate which is bound in a monolayer, a substrate or a precursor for a biomineralization reaction of the inorganic material-binding peptides; forming a biomineral layer by utilizing a biomineralization ability of the inorganic material-binding peptides; subsequently introducing onto a surface of the biomineral layer thus formed the aggregate having a binding ability to the biomineral layer; binding in a monolayer the aggregate which supports inorganic nanoparticles onto the biomineral layer by utilizing a binding ability of the inorganic material-binding peptides to the biomineral layer; and optionally, repeating one or more times the steps (b) and (a) of a multilayering operation: (b) introducing onto a surface of the aggregate which is bound in a monolayer, a substrate or a precursor for a biomineralization reaction of the inorganic material-binding peptides, and forming a biomineral layer by utilizing the biomineralizatin ability of the inorganic material-binding peptides; (a) introducing onto a surface of the biomineral layer thus formed the aggregate which supports inorganic nanoparticles having a binding ability to the biomineral layer, and binding the aggregate in a monolayer onto the biomineral layer by utilizing the binding ability of the inorganic material-binding peptides to the biomineral layer ("10")

The present invention further relates to: a three-dimensional structure of a functional material wherein, via an aggregate which is bound in a monolayer onto a surface of an inorganic substrate and is presenting on its surface a plurality of the same or different inorganic material-binding peptides, a substrate or a precursor for a biomineralization reaction of the inorganic material-binding peptides is formed as a biomineral layer by a biomineralization ability of the inorganic material-binding peptides, and further a multilayered structure of (a) and (b) is repeated one or more times: (a) via the aggregate which is bound in a monolayer onto a surface of the biomineral layer thus formed; (b) a substrate or a precursor for the biomineralization reaction of the inorganic material-binding peptides is formed as a biomineral layer by the biomineralization ability of the inorganic material-binding peptides ("11"); a three-dimensional structure of a functional material, wherein, via an aggregate which is bound in a monolayer onto a surface of an inorganic substrate and is presenting on its surface a plurality of the same or different inorganic material-binding peptides, a substrate or a precursor for a biomineralization reaction of the inorganic material-binding peptides is formed as a biomineral layer by a biomineralization ability of the inorganic material-binding peptides, and wherein the aggregate supporting an inorganic nanoparticle is bound in a monolayer onto a surface of the biomineral layer thus formed, and further, a multilayered structure of (b) and (a) is optionally repeated one or more times: (b) via the bound aggregate, a substrate or a precursor for the biomineralization reaction of the inorganic material-binding peptides is formed as a biomineral layer by the biomineralization ability of the inorganic material-binding peptides; (a) onto a surface of the biomineral layer thus formed, the aggregate which is supporting an inorganic nanoparticle is bound in a monolayer ("12"); the three-dimensional structure of a functional material according to "11" or "12", wherein the inorganic material-binding peptide is RKLPDA (SEQ ID NO:1) or RKLPDAPGMHTW (SEQ ID NO:2) ("13"); the three-dimensional structure of a functional material according to "11" or "12", wherein the inorganic material-binding peptide is a peptide consisting of an amino acid sequence that exists in nature ("14"); the three-dimensional structure of a functional material according to any one of "11" to "14", wherein the aggregate is a fusion protein complex in which a plurality of the same or different inorganic material-binding peptides are fused ("15"); the three-dimensional structure of a functional material according to "15", the three-dimensional structure of a functional material according to any one of "11" to "16", wherein the functional material is a semiconductor material or a semiconductor nanoparticle ("19"); and the three-dimensional structure of a functional material according to any one of "11" to "16", wherein the functional material is a metal-oxide material or a metal-oxide nanoparticle ("20").

BEST MODE OF CARRYING OUT THE INVENTION

Figure 1:
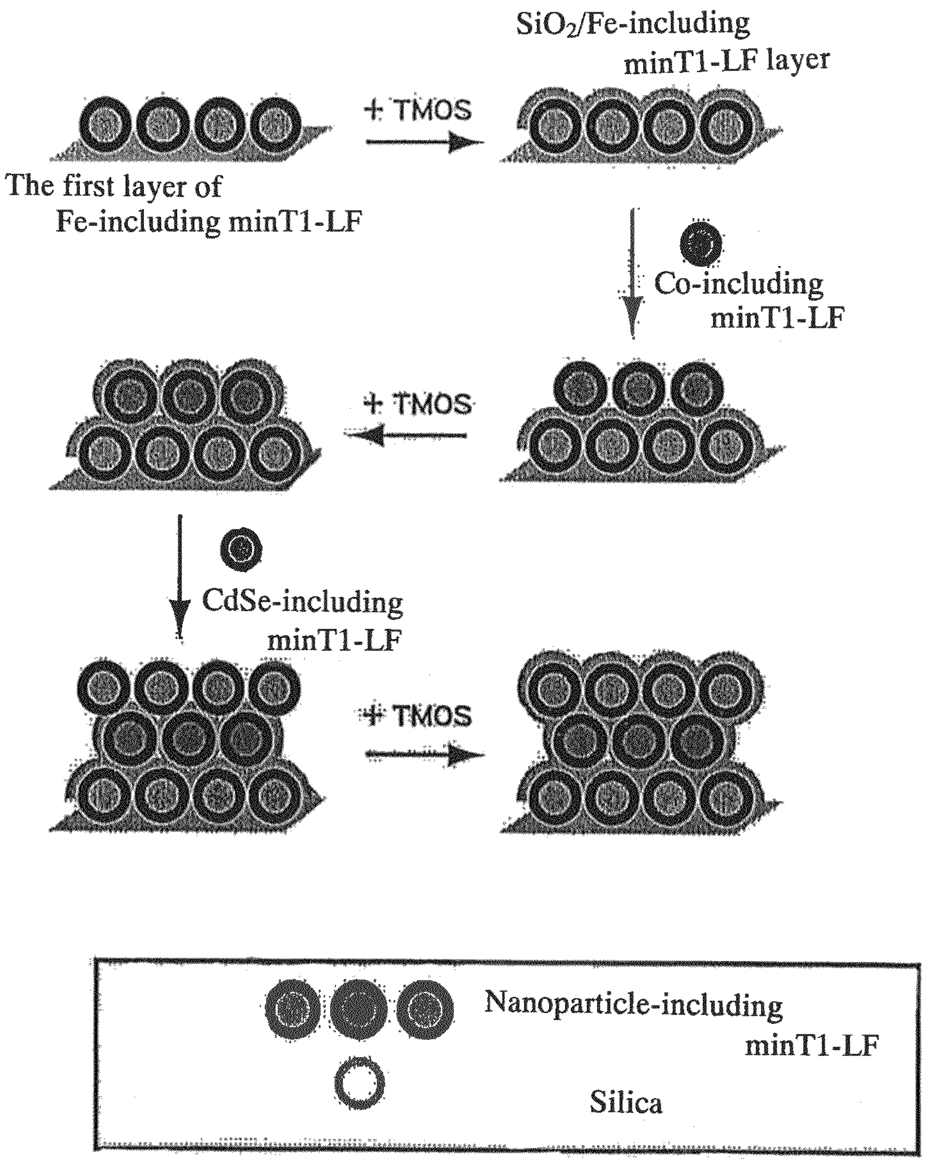
FIG. 1 This figure shows a frame format of the method utilizing minT1-LF for controlling a three-dimensional positioning of nanoparticles.

The method for manufacturing a monolayer thin film of an inorganic material of the present invention is not particularly limited as long as it is a method comprising the steps of introducing onto a surface of an inorganic substrate an aggregate presenting on its surface a plurality of the same or different inorganic material-binding peptides; binding the aggregate in a monolayer onto the inorganic substrate; introducing onto the aggregate which is bound in a monolayer, a substrate or a precursor for a biomineralization reaction of the inorganic material-binding peptides; and forming a biomineral layer utilizing a biomineralization ability of the inorganic material-binding peptides. Further, the monolayer thin film of an inorganic material of the present invention is not particularly limited as long as it is a monolayer thin film, wherein, via an aggregate which is bound in a monolayer onto a surface of an inorganic substrate and is presenting on its surface a plurality of the same or different inorganic material-binding peptides, a substrate or a precursor for a biomineralization reaction of the inorganic material-binding peptide is formed as a biomineral layer by a biomineralization ability of the inorganic material-binding peptide.

Furthermore, the method for manufacturing a three-dimensional structure of an inorganic material of the present invention is not particularly limited as long as it is a method comprising the steps of introducing onto a surface of an inorganic substrate an aggregate presenting on its surface a plurality of the same or different inorganic material-binding peptides; binding the aggregate in a monolayer onto the inorganic substrate; introducing onto the aggregate which is bound in a monolayer a substrate or a precursor for a biomineralization reaction of the inorganic material-binding peptides; forming a biomineral layer utilizing a biomineralization ability of the inorganic material-binding peptides; and subsequently repeating one or more times the steps (a) and (b) of a multilayering operation: (a) introducing onto the biomineral layer thus formed the aggregate having a binding ability to the biomineral layer, and binding the aggregate in a monolayer onto the biomineral layer by utilizing the binding ability of the inorganic material-binding peptides to the biomineral layer; (b) introducing onto the surface of the aggregate which is bound in a monolayer, a substrate or a precursor for a biomineralization reaction of the inorganic material-binding peptides, and forming a biomineral layer by utilizing the biomineralization ability of the inorganic material-binding peptides; or a method for manufacturing a three-dimensional structure of a functional material comprising the steps of introducing onto a surface of an inorganic substrate an aggregate presenting on its surface a plurality of the same or different inorganic material-binding peptides; binding the aggregate in a monolayer onto the inorganic substrate; introducing onto the aggregate which is bound in a monolayer, a substrate or a precursor for a biomineralization reaction of the inorganic material-binding peptides; forming a biomineral layer by utilizing a biomineralization ability of the inorganic material-binding peptides; subsequently introducing onto a surface of the biomineral layer thus formed the aggregate having a binding ability to the biomineral layer; binding in a monolayer the aggregate which supports inorganic nanoparticles onto the biomineral layer by utilizing a binding ability of the inorganic material-binding peptides to the biomineral layer; and optionally, repeating one or more times the steps (b) and (a) of a multilayering operation: (b) introducing onto a surface of the aggregate which is bound in a monolayer, a substrate or a precursor for a biomineralization reaction of the inorganic material-binding peptides, and forming a biomineral layer by utilizing the biomineralization ability of the inorganic material-binding peptides; (a) introducing onto a surface of the biomineral layer thus formed the aggregate which supports inorganic nanoparticles having a binding ability to the biomineral layer, and binding the aggregate in a monolayer onto the biomineral layer by utilizing the binding ability of the inorganic material-binding peptides to the biomineral layer.

Still further, a three-dimensional structure of a functional material of the present invention is not particularly limited as long as it is a structure, wherein, via an aggregate which is bound in a monolayer onto a surface of an inorganic substrate and is presenting on its surface the same or different inorganic material-binding peptides, a substrate or a precursor for a biomineralization reaction of the inorganic material-binding peptides is formed as a biomineral layer by a biomineralization ability of the inorganic material-binding peptides, and wherein a multilayered structure of (a) and (b) is repeated one or more times: (a) via the aggregate which is bound in a monolayer onto a surface of the biomineral layer thus formed; (b) a substrate or a precursor for a biomineralization reaction of the inorganic material-binding peptides is formed as a biomineral layer by the biomineralization ability of the inorganic material-binding peptide; or a three-dimensional structure of a functional material, wherein, via an aggregate which is bound in a monolayer onto a surface of an inorganic substrate and is presenting on its surface the same or different inorganic material-binding peptides, a substrate or precursor for a biomineralization reaction of the inorganic material-binding peptides is formed as a biomineral layer by a biomineralization ability of the inorganic material-binding peptides, and wherein the aggregate supporting an inorganic nanoparticle is bound in a monolayer onto a surface of the biomineral layer thus formed, and further a multilayered structure of (b) and (a) is repeated one or more times optionally: (b) via the bound aggregate, a substrate or a precursor for a biomineralization reaction of the inorganic material-binding peptides is formed as a biomineral layer by a biomineralization ability of the inorganic material-binding peptides; (a) the aggregate which is supporting an inorganic nanoparticle is bound in a monolayer onto a surface of the biomineral layer thus formed.

Examples of the above-mentioned inorganic substrate include, for example, substrates constituted by metals such as titanium, gold, silver, copper, silicon, aluminium, and stainless, or inorganic materials such as ceramics, almina, glass, quartz, mica, and silicone.

Examples of the inorganic material-binding peptide of the present invention include a peptide obtained artificially by a phage display method targeting an inorganic material, a peptide obtained artificially by a cell surface display method targeting an inorganic material, and a peptide consisting of an amino acid sequence that exists in nature. As the above inorganic materials, inorganic elements (Ti, Si, Fe, Co, Zn, Ni, As, Ag, Pt, Pd, Au, Al, Mn, W, Ge, P, C and the like) and inorganic compounds ($TiO_2$, GaAs, $CaCO_3$, $SiO_2$, ZnS, $Fe_2O_3$, $Cr_2O_3$, $PbO_2$, CoO, $MnO_2$, zeolites and the like) can be specifically exemplified.

Examples of a method for obtaining a peptide having an ability to bind titanium artificially by a phage display method include, a method comprising the steps of allowing to contact, preferably in an aqueous solution, titanium with peptide sequences on the phage particles; recovering by a centrifugal operation the titanium to which a phage particle is bound via the peptide sequence; proliferating in bacteria such as *Escherichia coli* the obtained phage particle bound to titanium; and subsequently repeating a panning operation of contacting titanium and the proliferated phage population that displays the peptide sequence on the phage particles; thereby concentrating phage clones that bind to titanium. As the above-mentioned titanium, titanium such as metal titanium in the form of a particle or plate, titanium alloy, and titanium dioxide can be used. Further, the above-mentioned phage library can be prepared as a phage displaying on its surface layer the amino acid residue (-Xn-, X=any amino acid) of the randomized portion by inserting a chemically synthesized random DNA into a phage DNA (phagemid) and introducing the DNA to host *Escherichia coli*, so that a molecule is biosynthesized to form a phage virus, and a random peptide is expressed at the tip of N-terminal of pIII which is an outer-shell protein of a viral particle. Meanwhile, commercially available phage libraries (random 7 mer, 12 mer, cyclic 7 mer and like) can also be used.

Specific examples of thus obtained peptides having a binding ability to titanium include RKLPDA (SEQ ID NO:1), RKLPDAPGMHTW (SEQ ID NO:2), RALPDA (SEQ ID NO:3) and the like. Further, metal titanium, titanium alloy, amorphous titanium dioxide, anatase crystals of titanium dioxide, rutile crystals of titanium dioxide, and brookite crystals of titanium dioxide can be exemplified as titanium. Furthermore, specific examples of peptides having a binding ability to a nanographite structure include DYFSSPYYEQLF (SEQ ID NO: 4) and YDPFHII (SEQ ID NO:5).

In addition, examples of peptides having a binding ability to GaAs include AQNPSDNNTHTH (SEQ ID NO:6), RLELAIPLQGSG (SEQ ID NO:7), and TPPRPIQYNHTS (SEQ ID NO:8) as described previously in [(Whaley et al., 2000) Whaley, S. R., English, D. S., Hu, E. L., Barbara, P. F., and Belcher, A. M. (2000). Selection of peptides with semiconductor binding specificity for directed nanocrystal assembly. Nature 405, 665-668]. Examples of peptides having a binding ability to $CaCO_3$ include HTQNMRMYEPWF (SEQ ID NO:9) and DVFSSFNLKHMR (SEQ ID NO:10) as described previously in [Gaskin, D. J. H., Starck, K., and Vulfson, E. N. (2000). Identification of inorganic crystal-specific sequences using phage display combinatorial library of short peptides: A feasibility study. Biotech Lett 22, 1211-1216]. Examples of peptides having a binding ability to Ag include AYSSGAPPMPPF (SEQ ID NO:11), NPSSLFRYLPSD (SEQ ID NO:12), and SLATQPPRTPPV (SEQ ID NO:13) as described previously in [Naik, R. R., Stringer, S. J., Agarwal, G., Jones, S. E., and Stone, M. O. (2002b). Biomimetic synthesis and patterning of silver nanoparticles. Nat Mater 1, 169-172].

Further, examples of peptides having a binding ability to $SiO_2$ include MSPHPHPRHHHT (SEQ ID NO:14), RGRRRRLSCRLL (SEQ ID NO:15), and KPSHHHHHTGAN (SEQ ID NO:16) as described previouslyin [Naik, R. R., Brott, L. L., Clarson, S. J., and Stone, M. O. (2002a). Silica-precipitating peptides isolated from a combinatorial phage display peptide library. J Nanosci Nanotechnol 2, 95-100]. Examples of peptides having a binding ability to ZnS include CNNPMHQNC (SEQ ID NO:17) as described previously in [Lee, S. W., Mao, C., Flynn, C. E., and Belcher, A. M. (2002). Ordering of quantum dots using genetically engineered viruses. Science 296, 892-295]. Examples of peptides having a binding ability to Pt include CDRTSTWRC (SEQ ID NO:18), CQSVRSTKC (SEQ ID NO:19), and CSSSHLNKC (SEQ ID NO:20) as described previously in [Sarikaya, M., Tamerler, C., Jen, A. K., Schulten, K., and Baneyx, F. (2003). Molecular biomimetics: nanotechnology through biology. Nat Mater 2, 577-585]. Examples of peptides having a binding ability to Pd include CSVTQNKYC (SEQ ID NO:21), CSPHPGPYC (SEQ ID NO:22), and CHAPTPMLC (SEQ ID NO:23).

Still further, examples of peptides having a binding ability to $Fe_2O_3$ include RRTVKHHVN (SEQ ID NO:24) as described previously in [Brown, S. (1992). Engineered iron oxide-adhesion mutants of the *Escherichia coli* phage lambda receptor. Proc Natl Acad Sci USA 89, 8651-8655]. Examples of peptides having a binding ability to Au include MHGKTQATSGTIQS (SEQ ID NO:25), LGQSGQSLQGSEKTNG (SEQ ID NO:26), and EKLVRGMEGASLHPA (SEQ ID NO:27) as described previously in [Brown, S. (1997). Metal-recognition by repeating polypeptides. Nat Biotechnol 15, 269-272]. Examples of peptides having a binding ability to $Cr_2O_3$ include VVRPKAATN (SEQ ID NO:28) and RIRHRLVGQ (SEQ ID NO:29) as described previously in [Schembri, M. A., Kjaergaard, K., and Klemm, P. (1991). Bioaccumulation of heavy metals by fimbrial designer adhesins. FEMS Microbiol Lett 170, 363-371]. Examples of peptides having a binding ability to $PbO_2$ include YPPFHNNDHRS (SEQ ID NO:30) and SKPLARSSGA (SEQ ID NO:31). Examples of peptides having a binding ability to CoO include GRMQRRVAH (SEQ ID NO:32) and LGKDRPHFHRS (SEQ ID NO:33). Examples of peptides having a binding ability to $MnO_2$ include HHMLRRRNT (SEQ ID NO:34) and HINASQRVA (SEQ ID NO:35).

Furthermore, examples of peptides having a binding ability to ZnO include TRRGTHNKD (SEQ ID NO:36) and NTRMTARQHRSANHKSTQRARS (SEQ ID NO:37) as described previously in [Kjaergaad, K., Sørensen, J. K., Schembri, M. A., and Klemm, P. (2000). Sequestration of zinc oxide by fimbrial designer chelators. Appl Environ Microbiol 66, 10-14]. Examples of peptides having a binding ability to zeolites include MDHGKYRQKQATPG (SEQ ID NO:38) and VKTQATSREEPPRLPSKHRPG (SEQ ID NO:39) as described previously in [Nygaard, S., Wendelbo, R., and Brown, S. (2002). Surface-specific zeolite-binding proteins. Adv Mater 14, 1853-1856].

Such peptides having a binding ability to an inorganic material can be manufactured according to their amino acid sequences by a general chemical synthesis method. Such chemical synthesis method encompasses peptide synthesis methods by a common liquid-phase method and a solid-phase method. More specifically, such peptide synthesis method encompasses a stepwise elongation method comprising the step of binding each amino acid successively one by one based on the information of the amino-acid sequence to elongate a chain; and a fragment condensation method comprising the step of synthesizing in advance fragments consisting of several amino acids and subsequently performing a coupling reaction of each fragment.

Further, as a method for artificially obtaining an inorganic material-binding peptide by a cell surface display method targeting an inorganic material, the method previously described in [Brown, S. (1992). Engineered iron oxide-adhesion mutants of the *Escherichia coli* phage lambda receptor. Proc Natl Acad Sci USA 89, 8651-8655] can be specifically exemplified.

Examples of an inorganic material-binding peptide consisting of an amino acid sequence that exists in nature include a peptide derived from a diatom protein and a peptide derived from a protein related to a biomineralization that exists in nature. Examples of the above-mentioned diatom protein include Silicatein α Tethya aurantia (Shimizu et al., 1998), Silicatein β Tethya aurantia (Accession No: AAF21819), Silicatein a Halichondria okadai (Accession No: BAB86343), and Silaffin 1 precursor (natSil-1) Cylindrotheca fusiformis (Accession No: Q9SE35). As a peptide derived form a diatom protein, partial peptide R5 (SSKKSGSYSGSKGSKRRIL; SEQ ID NO:4) of the above Silaffin 1 can be specifically exemplified. In addition, examples of a protein related to a biomineralization that exists in nature include rat-derived DMP-1 (dentin matrix protein 1) involved in osteogenesis described previously in [Bone 34 (6), (2004)], human-derived enamelin involved in the formation of the enamel layer of a tooth described previously in [J. Dent. Res. 81 (11), 738-742 (2002)], and human-derived amelogenin (Y chromosome) precursor involved in the formation of an enamel layer described previously in [Nature 423 (6942), (2003)]. It is reported that a biomineralization of apatite occurs in the co-presence of the DMP-1-derived partial peptides pA (ESQES; SEQ ID NO: 40) and pB (QESQSEQDS; SEQ ID NO: 41) (Nature Materials 2 p 552).

Further, as the above-mentioned inorganic material-binding peptide, a chemically-modified inorganic material-binding peptide can be advantageously used. Examples of such chemical modification include a chemical modification consisting of a substitution into an amino acid having a functional group; and a chemical modification for facilitating the formation of a linkage with a linker. However, a preferred modification does not result in a decreased binding ability to an inorganic material such as titanium due to the chemical modification. Examples of the above-mentioned chemical modification for facilitating the formation of a linkage with a linker include a covalent binding of biotin to an amino acid group of a peptide using N-hydroxysuccinimide ester of biotin. The biotinilation of the peptide can facilitate the production of a chimeric molecule.

Next, as an aggregate presenting on its surface a plurality of the same or different inorganic material-binding peptides, the followings can be exemplified: a fusion protein complex consisting of a plurality of the same or different inorganic material-binding peptides and a protein to which the peptide is fused, preferably at the N-terminal of the protein; a chemically modified protein consisting of a plurality of the same or different inorganic material-binding peptides and a protein to which the peptides are bound, preferably by a covalent binding; and a peptide-bound organic high molecular compound consisting of a plurality of the same or different inorganic material-binding peptides and an organic high molecular compound to which the peptides are bound, preferably by a covalent binding; as well as a biotin-avidin complex, an antigenic protein-antibody complex. Inorganic materials such as metal nanoparticles, semiconductor materials, focusing elements, fluorescent molecules can be supported on the aggregate by an inclusion, conjugation, chemical modification, or adsorption.

Examples of the above-mentioned fusion protein complex include a multimeric protein complex, a protein complex having a core-shell structure, a ferritin protein complex derived from a higher eukaryote, an iron-storage protein complex derived from bacteria, and a viral particle or a viral outer-shell protein complex. Examples of a multimeric protein and a protein having a core-shell structure include members of the ferritin protein family such as ferritin or apoferritin derived from a higher eukaryote; iron-storage proteins such as DpsA protein and MrgA protein derived from bacteria; a viral particle or a viral outer-shell protein such as adenovirus, rotavirus, poliovirus, HK97, cytomegalovirus, tobacco mosaic virus, cowpea mosaic virus (CPMV), cowpea chlorotic mottle virus (CCMV) and M13 bacteriophage; a GroEL complex and a GroEL-GroES complex. For example, an adenovirus particle of a regular icosahedron is a heteromultimeric protein, and a method for chemically modifying a viral particle such as an adenovirus particle and a viral outer-shell protein is well known (Chemistry and Biology 2002, Vol. 9 p 805-811, Journal of Nanobiotechnology 2003, 1; 5, Journal of American Chemical Society 2003, Vol. 125, p 6848-6849). Further, a GroEL-GroES complex is a pot hat-shaped, very large structure consisting of 60000 atoms. In the complex, 7 GroEL molecules makes a torus-shaped ring, and 2 such rings (14 GroELs in total) form the lower part of the hat which is 140 Å in diameter and 150 Å in height. 7 GroES molecules are bound to close the hat in the upper part of the hat which is 80 Å in diameter and 30 Å in height. This brings the total height of the complex to about 185 Å. In the complex, there is a large tubular cavity which is 50 Å to 60 Å in diameter and about 150 Å in length along the 7-fold symmetric axis, and at the top of the hat, there is a round-shaped hole which is 10 Å in diameter. The cavity is of the size for a protein to fit easily so that the protein can interact with the residues on the inner surface of the cavity. Among such complexes, for example, type L ferritins such as horse-spleen derived type L ferritin, or type H ferritins derived from a higher eucaryote can be preferably exemplified.

Further, examples of a chemically modified protein consisting of a plurality of the same or different inorganic material-binding peptides and a protein which is chemically modified (bound) with the peptide, preferably by a covalent binding, include a chemically modified protein, wherein the inorganic material-binding peptides are covalently bound to proteins such as members of the ferritin protein family like a higher eukaryote-derived firritin and apoferritin, luciferase, amylase, lipase, catalase, beta-lactamase, phosphofructokinase, myosin, kinesin, integrin, rhodopsin, bacterio-rhodopsin, G-protein-coupled proteins, G-protein group, and G-protein group of low molecular-weight and the like such as Ras, Ran, and CDC42, by an ordinary method such as those described in Examples; and chemically modified proteins in which the above-mentioned chemically-modified inorganic material-binding peptide is bound.

Furthermore, examples of the above mentioned aggregate consisting of an organic high molecular compound which is chemically modified (bound) with a plurality of the same or different inorganic material-binding peptides includes a block copolymer of a hydrophobic block and a hydrophilic block to which a plurality of the same or different inorganic material-binding peptides are bound; and hyperbranched polymers such as a dendrimer wherein a plurality of the same or different inorganic material-binding peptides are bound to branch tips and a star polymer wherein a plurality of the same or different inorganic material-binding peptides are bound to arm tips.

The above mentioned hydrophobic block in a block copolymer is selected from the group consisting of polyester, polystyrene, polyamino acid, polyortho ester, and polyphosphagene. More preferably, the hydrophobic block can be selected from the group consisting of poly-L-leucine, poly-L-isoleucine, poly-L-valine, poly-L-phenylalanine, polylactide, polyglycolide, polycaprolactone, polydioxane-2-on, polylactic-co-glycolide, polylactic-co-dioxane-2-on, polylactic-co-caprolactone, and polyglycolic-co-caprolactone. The carboxyl end group of the above mentioned hydrophobic block can be substituted for a fatty acid such as a butyric acid group, propionic acid group, acetic acid group, stearic acid group, or pulmitic acid group. The number average molecular weight of hydrophobic blocks is 500 to 50,000 daltons, among which, 500 to 20,000 daltons is preferred.

Further, the above hydrophilic block in the block copolymer, to which a plurality of the same or different inorganic material-binding peptides are bound, is selected from the group consisting of polyamino acid, polyalkylene glycol, polyvinyl alcohol, polyvinyl pyrolidone or polyacrylamide, and derivatives thereof. More preferably, the hydrophilic block can be selected from the group consisting of poly-L-serine, poly-L-threonine, poly-L-lysine, poly-L-arginine, poly-L-asparaginic acid, poly-L-glutamic acid, poly-L-asparagine, poly-L-glutamine, monomethoxypolyethylene glycol, monoacetoxypolyethylene glycol, polyethylene glycol, polyethylene-co-propylene glycol, and polyvinyl pyrolidone. The number average molecular weight of hydrophilic blocks is 500 to 50,000 daltons, among which, 500 to 20,000 daltons is preferred. An inorganic material-binding peptide is capable of binding to a hydrophilic block via a functional group such as an amino group or carboxyl group of the hydrophilic block. Alternatively, by adding a cysteine residue to an inorganic material-binding peptide, the peptide can be bound to a hydrophilic block via a tiol group of the cysteine residue.

Specifically, the followings can be exemplified: a diblock copolymer consisting of polylactide and polyalkylene glycol to which inorganic material-binding peptides are bound; a diblock copolymer consisting of polyethyleneimine to which inorganic material-binding peptides are bound and aliphatic polyester; a triblock copolymer consisting of a polyoxyethylene block to which inorganic material-binding peptide are bound, a polyoxypropyrene block, and a polyoxyethylene block to which inorganic material-binding peptides are bound; and a triblock copolymer consisting of polylactide, poly(ethylene oxide) to which inorganic material-binding peptides are bound, and polylactide. For example, acetal-poly (ethylene glycol)-block-[poly(2-(N,N-dimethylamino)ethyl methacrylate)] (Acetal-PEG/PAMA) can be preferably exemplified. Further, in the aqueous phase, a diblock copolymer consisting of a hydrophilic block and a hydrophobic block forms a high molecular micelle of a core-shell form in which the hydrophobic block forms a core and the hydrophilic block forms a shell. For example, a preparation of a polymer of a hydrophobic block, a hydrophilic block, and inorganic material-binding peptides provides an aggregate presenting a plurality of inorganic material-binding peptides on the micelle surface. In addition, inorganic nanoparticles can be supported within such micelle of a block copolymer by an ordinary method.

A dendrimer or star polymer used in the present invention can be any dendrimer or star polymer including known dendrimers and star polymers, as long as it can bind, preferably by a covalent binding, a plurality of the same or different inorganic material-binding peptides at the tip of a plurality of branches or at the tip of a plurality of arms. In organic material-binding peptides can be chemically bound to a dendrimer or star polymer via a functional group such as an amino group or carboxyl group at the tip of branches or at the tip or arms by an ordinary method. As these dendrimers or star polymers the followings can also be used: sugar, monohydroxyl and oligohydroxyl C1-C6 alkyl, monohydroxyl and oligohydroxyl C2-C6 acyl, C1-C2 alkoxyalkyl capable of having one or more hydroxyl group substituted for alkoxy group or alkylene group, amino acid, peptide, oligo such as polyoxyethylene consisting of 1 to 120 ethylene oxide units, or derivatives chemically modified with a hydrophilic group such as poly-(oxa C1-C3 alkylene).

Examples of a substrate or a precursor for a biomineralization reaction of an inorganic material-binding peptide include a metallic chloride, metallic ammonium salt, metallic carbonate, and metallic nitrate salt such as silver nitrite, copper, $HAuCl_3$, iron chloride, $H_2PtCl_6$ and ammonium iron; selenourea and urea sulfide; and metallic alkoxides such as tetramethoxysilane, tetraethoxysilane, and tetrabutoxytitanium, or a hydrolytic product of a metallic alkoxide. These are converted by an inorganic material-binding peptide into an insoluble form in water, such as solid silver and CuS. Herein, the term “biomineralization ability” means an ability to produce a mineral in the same manner as it is generated in vivo (a mineralization ability), and the produced mineral layer is called a biomineral layer. A monolayer thin film of an inorganic material of the present invention is formed as a monolayer of the biomineral layer, which can be preferably exemplified by a monolayer of silica or silica-containing molecules and a monolayer of titanium dioxide, preferably a monolayer of titanium dioxide with a photocatalytic ability.

A functional material in the present invention is not particularly limited as long as it is a material constituted by an inorganic substance, which can be exemplified by a thin film of an inorganic material such as a thin film of silica or silica-containing molecules and a thin film of titanium dioxide, preferably a thin film of titanium dioxide with a photocatalytic ability; an organic material with a specific function such as a semiconductor; a metal material and its oxide, chloride, hydroxide, or carbonate; a carbon material such as a diamond; and an inorganic nanoparticle such as a metallic nanoparticle. Examples of the above-mentioned metal material include Au, Ag, Pd, Pt, Cu, Ni, Co, Fe, Mn, P, Be, Ga, Pb, Zn, Cd, and Cr, and examples of a metallic nanoparticle include nanoparticles of these metal materials. Further, examples of an oxidative metal material include SnO, $Sb_2O_3$, ZnO, $In_2O_3$, $Ga_2O_3$, $Fe_2O_3$, $Ag_2O$, $TiO_2$, $SiO_2$ and alloys thereof, and examples of an oxidative metal nanoparticle include nanoparticles of these oxidative metal materials. Examples of a metal chloride material include CuCl, $FeCl_2$, $PtCl_2$, $CoCl_2$, $NiCl_2$, $MnCl_2$, $PdCl_2$, $SbCl_3$, and $CrCl_3$, and examples of a metal chloride nanoparticle include nanoparticles of these metal chloride materials.

Further, examples of the above-mentioned semiconductor material include Ge, Si, SiGe, ZnO, ZnS, ZnSe, ZnTe, CdO, CdS, CdMnS, CdSe, CdMnSe, CdTe, CdMnTe, HgS, HgSe, HgTe, InP, InAs, InSb, InN, GaN, GaP, GaAs, GaSb, $TiO_2$, $WO_3$, PbS, PbSe, MgTe, AlAs, AlP, AlSb, AlS, CdZnS, CdZnSe, CdZnTe, PbTe, $Cd_3P_2$, $Cd_3As_2$, $Zn_3P_2$, $Zn_3As_2$, $In_2S_3$, $CuInS_2$, $In_2Se_3$, $CuInSe_2$, $In_2O_3$, MgTe, AlAs, AlP, AlSb, and AlS, and examples of a semiconductor nanoparticle include nanoparticles of these semiconductor materials. In addition, it is also possible to align an electron-donating group such as —OH, —$OCH_3$, and —$NH_2$ on the core surface of a semiconductor nanoparticle to provide a semiconductor nanoparticle with a fluorescence property.

The above-mentioned inorganic nanoparticles are used while being supported inside the above-mentioned ferritin protein complex, viral particle or viral outer-shell protein complex, protein complex with a core-shell structure, block copolymer of a hydrophobic block and a hydrophilic block to which a plurality of the same or different inorganic material-binding peptides are bound, dendrimer wherein a plurality of the same or different inorganic material-binding peptides are bound to branch tips, and the like.

A three-dimensional structure of a functional material of the present invention can be any three-dimensional structure of the above-mentioned functional materials. Put into patterns, the followings can be exemplified: a three dimensional structure of a multilayered thin films wherein thin films of an inorganic material such as thin films of silica or silica-containing molecules or thin films of titanium dioxide are multilayered; and a three-dimensional structure in which a positioning is controlled and which is formed by the steps of modifying a substrate with plural kinds of inorganic materials, binding in a monolayer an aggregate presenting on its surface a plurality of the same or different inorganic material-binding peptides by "a direct patterning", only to the specific region which is modified with inorganic peptides; forming a biomineral layer by utilizing a biomineralization ability of the inorganic material-binding peptides; forming a multilayer by utilizing the binding ability of the inorganic material-binding peptides to the biomineral layer thus formed; thereby positioning the inorganic material three-dimensionally. Further, when seen cross sectionally, a three-dimensional can be exemplified by a three dimensional structure consisting of multilayered thin films, a three dimensional structure in which inorganic nanoparticles such as metal nanoparticles are present between respective thin films (a sandwich structure), and a three dimensional structure in which inorganic nanoparticles are present on the outer surface of a monolayer thin film, multilayered thin films, or a sandwich structure.

Since it is possible to apply a coating of avidin around semiconductor nanoparticles, three-dimensional structures can be stratified by applying a coating of biotin-avidin complex fused with inorganic material-binding peptides around the semiconductor nanoparticles. Further, with antigenic protein-antibody complex, three-dimensional structures can be stratified by making a three-dimensional structure using ferritin fused with titanium-binding peptides so that the biomineral layer would be titanium dioxide; making the top layer a ferritin layer; binding anti-ferritin antibody fused with cobalt-oxide binding peptides to the ferritin of the top layer to produce an antibody layer; subsequently performing a biomineralization of cobalt oxide to produce a cobalt-oxide layer; binding ferritin fused with cobalt oxide-binding peptides to the cobalt oxide layer; and carrying on the same steps so that the biomineral layer would be cobalt oxide.

Hereinafter, the present invention will be explained more specifically with reference to the following examples, while the technical scope of the present invention will not be limited to these exemplifications.

Example 1

Preparation of a Fusion Protein minT1-LF Wherein Inorganic Material-Binding Peptides are Fused The production of a DNA (pKIS1) for expressing a fusion ferritin protein (minT1-LF), wherein a horse spleen-derived type L ferritin (LF) is fused with a titanium-binding peptide (minTBP-1) consisting of the amino acid sequence shown by SEQ ID NO: 1, was performed in accordance with the following procedures. In brief, an annealing reaction was performed by: mixing 100 pmole/μl each of synthetic DNAs of SEQ ID NOs: 43 (sequence 5'-GATCCATGCGCAAACTTCCGGATGCGAGCT-3') and 44 (sequence 5'-CGCATCCGGAAGTTTGCGCATG-3') which are complementary to each other and encode Met, an initiation codon, and subsequently encode the amino acid sequence shown by SEQ ID NO: 42, and have a restriction enzyme BamHI linker sequence on the initiation codon side and a restriction enzyme SalI linker sequence on the opposite side, in 50 mM NaCl, 10 mM Tris-HCl, and 10 mM $MgCl_2$; heating the resultant mixture at 70° C. for 10 minutes; and then slowly cooling the mixture to room temperature. Then, cDNA of horse spleen-derived type L ferritin digested a plasmid pKITO which had been cloned into the downstream of tac promoter (Okuda et al. 2003, Biotechnology and Bioengineering, Vol 84, No. 2, p 187-194) with restriction enzymes BamHI and SalI; a large DNA fragment, about 6 kb, separated by a 1% agarose gel electrophoresis was purified with Gene Clean II kit (BIO101); and the purified substance was mixed with the above-mentioned annealed DNA, and ligated by using T4 DNA ligase.

Next, this DNA and pKITO were each digested with BamHI, and DNA fragments separated by a 1% agarose gel electrophoresis, the former was a fragment of about 6 kb, and the latter was a fragment of about 300 bp, were purified with Gene Clean II kit (BIO101), and the purified substances were ligated using T4 DNA ligase. The bound DNA was cloned into *Escherichia coli* XLI-blue strain (hsdR17, supE44, recAl, endAl, gyrA46, thi, relAl, lac/F' [proAB+, lacIqΔ (lacZ) M15::Tn10 (tetR)]) in accordance with an ordinary method (Molecular Cloning Third Edition, Cold Spring Harbor Laboratory Press), and a clone into which a BamHI fragment of about 300 bp was inserted in the desired direction was determined by a dideoxy termination method (CEQ DTCS Quick start kit, Beckman, Calif.), through a DNA sequencing with the use of a primer (SEQ ID NO: 45; 5'-GTGGAATTGTGAGCG-3') in a BamHI fragment of about 300 bp from pKITO. For the migration and data analysis of the reactant, an automated capillary sequencer (CEQ2000, Beckman) was used.

The fusion ferritin protein consisting of the amino acid sequence shown by SEQ ID NO: 46, wherein a horse spleen-derived type L ferritin is fused with a titanium-binding peptide, was expressed and purified as follows. In brief, the *Escherichia coli* XLI-blue strain was transformed with pKIS1 in accordance with an ordinary method, and a colony was picked up with a sterilized pick and shaking-cultured in 5 ml of LB medium at 37° C. for 16 to 18 hours. Then this culture solution was transplanted to 1 litter of LB medium and shaking-culture was performed at 37° C. for another 16 to 18 hours. *Escherichia coli* was harvested by a centrifugation (Beckman J2-21M, JA-14 rotor, 5000 rpm, 5 minutes). The *Escherichia coli* thus harvested was washed with 80 ml of 50 mM Tris-HCl (pH 8.0), and harvested by a centrifugation (Kubota, 5922, RA410M2 rotor, 4000 rpm, 10 minutes) again. The harvested *Escherichia coli* was suspended in 30 ml of 50 mM Tris-HCl (pH8.0), and then a solution of disrupted *Escherichia coli* cells was obtained by using an ultrasonic disruptor (BRANSON, SONIFIER 250, microtip, output level maximum, duty cycle 50%, 2 minutes; this procedure was repeated 3 to 4 times). The solution of disrupted *Eshcerichia coli* cells was subjected to a centrifugation (Kubota, 5922, RA410M2 rotor, 8000 rpm, 30 minutes) to collect soluble fractions. By putting the fractions into a warm bath at 65° C. for 20 minutes, coexisting proteins were denatured. The denatured coexisting proteins which formed precipitates were removed by a centrifugation (Kubota, 5922, RA410M2 rotor, 8000 rpm, 30 minutes), and the supernatant was collected.

The supernatant was poured into Q-sepharose HP (Amersham) which is a carrier for anion exchange chromatography, equilibrated with 50 mM Tris-HCl (pH 8.0), and the elution was performed with 100 ml of 100 to 500 mM sodium chloride concentration gradient (3 ml/min). About 40 ml of fractions containing minT1-LF was concentrated by Centriprep 10 (Amicon) to 2.5 to 3 ml, and the resultant was poured into a 60 cm-long gel filtration chromatograph Sephacryl S-400 equilibrated with 50 mM Tris-HCl (pH 8.0), 150 mM NaCl (herein after referred to as TBS), and a chromatography was performed at the flow rate of 1.5 ml/min. Each 100 μl fraction containing minT1-LF was poured into an SW4000XL column equilibrated with 50 mM Tris-HCl (pH7.5), 150 mM NaCl, 1 mM $NaN_3$, and was analyzed by chromatography at the flow rate of 1 ml/min to confirm that the purity of minT1-LF 24-mer was 95% or more. The minT1-LF was then used for the experiment described below.

Example 2

Manufacture of a Three-Dimensional Structure (a Method for Controlling a Three-Dimensional Positioning or a Method for Producing a Thin Film)—Specific FIG. 1 shows a schematic view of a method for manufacturing a three-dimensional structure (a method for controlling a three-dimensional positioning or a method for producing a thin film) utilizing the multifunctionality of mimTBP-1 of SEQ ID NO: 1 with the use of the protein model minT1-LF obtained in Example 1. QCM-D300 (q-sense AB, Goteborg), a quartz-crystal biomolecule interaction analyzer, was used to study the three dimensional structure. As a quartz crystal, a titanium sensor which was a genuine part for QCM-D300 was used. The temperature was set at 25.36 to 40° C. The actual measurement temperature was about 24.97° C. to 25.00° C.

Figure 2:
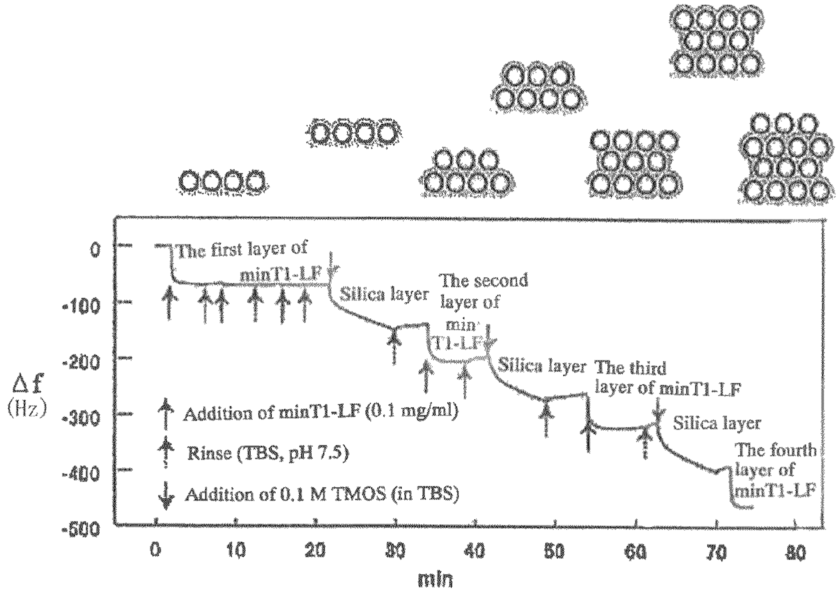
FIG. 2 This figure shows the controlling of a three-dimensional positioning of minT1-LF onto a titanium-coated QCM sensor. Firstly, when minT1-LF was repeatedly added, no change was observed in weight of the surface of the titanium sensor. This demonstrates that, with a conventional method, minT1-LF can only form a monolayer thin film on a titanium sensor. However, by utilizing the silica-forming ability of the minTBP-1 sequence of minT1-LF, a three-dimensional positioning of minT1-LF was successfully performed.

After the reference value was measured with 50 mM Tris-HCl (pH 7.5) and 150 mM NaCl (TBS), minT1-LF adjusted to the concentration of 0.1 mg/ml was introduced into the measurement chamber and was measured in succession. As shown in FIG. 2, a reduction in frequency by about 60 to 70 Hz was observed, which was associated with the binding of minT1-LF to the titanium substrate. After the sensor was stabilized, the inside of the chamber was rinsed with TBS. Again, 0.1 mg/ml of minT1-LF was introduced into the measurement chamber, but no significant frequency change that had been observed earlier was observed. This demonstrates that minT1-LF has formed a monolayer film on the titanium sensor. Then the inside of the chamber was rinsed again with TBS, and TBS added with 1/10 volume of 1M tetramethoxysilane (TMOS) pre-hydrolyzed with 1 mM hydrochloric acid was introduced into the measurement chamber. From the frequency change shown by QCM-D300, it is possible to monitor the process that silica layer is slowly depositing on the minT1-LF film by minT1-LF's ability to biomineralize silica. After a brief incubation, inside of the chamber was rinsed with TBS, and 0.1 mg/ml of minT1-LF was further introduced into the measurement chamber. This time, a reduction in frequency by about 60 Hz was observed in association with the binding of minT1-LF to the silica layer due to the silica-binding ability of minTBP-1. This means that the second layer of minT1-LF was formed. By repeating the above processes, minT1-LF was successfully positioned three-dimensionally.

From the above results, it was confirmed that the method for controlling a three-dimensional positioning and the method for forming a thin film utilizing the multi-functionality of an inorganic material-binding peptide were effective.

Example 3

Figure 3:
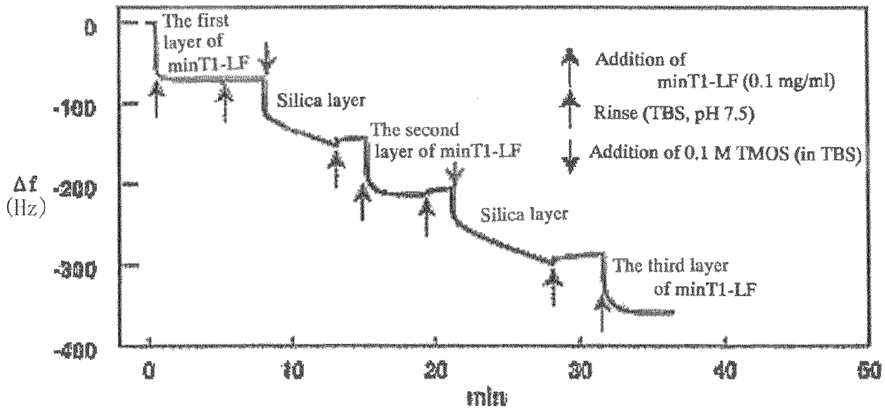
FIG. 3 This figure shows the controlling of a three-dimensional positioning of minT1-LF onto a gold-coated QCM sensor. It is shown by this figure that the method for controlling a three-dimensional positioning still functions even if the manner of minT1-LF adsorption in the first layer is a nonspecific adsorption (physical adsorption). Generally, ferritin is known to form a monolayer thin film by a nonspecific adsorption in the absence of a nonspecific-adsorption inhibitor such as a surfactant.

Manufacture of a Three-Dimensional Structure (a Method for Controlling a Three-Dimensional Positioning or a Method for Producing a Thin Film)—Nonspecific To confirm that the controlling of a three-dimensional positioning and the production of a thin film are also possible even if the binding form of minT1-LF in the first layer of Example 2 is a non-specific adsorption, a study was performed with a measurement by QCM-D300 (q-sense AB, Goteborg), a quartz-crystal biomolecule interaction analyzer, with the use of a gold-coated sensor in place of a titanium sensor. This time, the interaction between minT1-LF of the first layer and the gold sensor was a non-specific binding. The experiment was performed in exactly the same manner as in Example 2. Consequently, minT1-LF was successfully positioned three-dimensionally as shown in FIG. 3.

Figure 4:
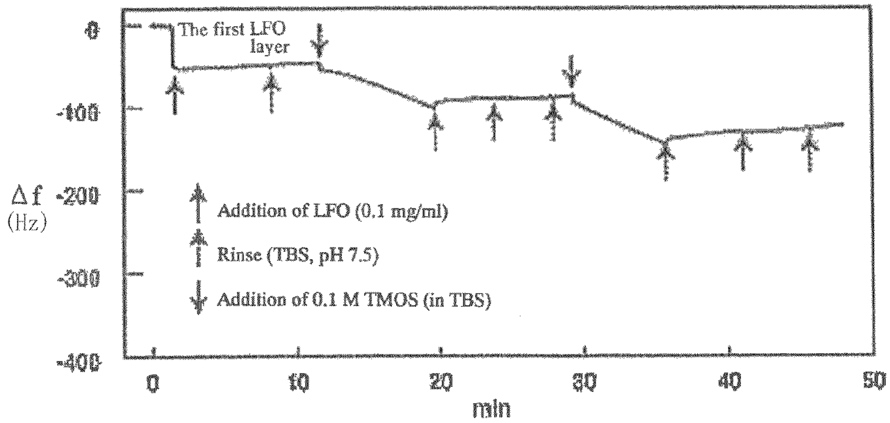
FIG. 4 This figure shows the result of a control experiment using LFO. Ferritin without the minTBP-1 sequence forms a monolayer thin film on a gold substrate by a nonspecific adsorption, but cannot be positioned three dimensionally due to lack of multifunctionality that an inorganic material-binding peptide has.

As a control experiment, the same experiment was performed using horse-L ferritin (LFO) not fused with inorganic material-binding peptides. Consequently, it was confirmed that a stratification of ferritin did not occur (FIG. 4).

From the above results, it was confirmed that, even if the interaction between the underlying substrate and the first layer was a nonspecific binding in the method for controlling a three-dimensional positioning or the method for forming a thin film, these methods would work similarly as in the case of a specific binding. This shows that a variety of selections are available for an underlying substrate according to the need.

Example 4

Formation of Nanoparticles

Ferritin has a core-shell structure and has an ability to form in its interior space a nanoparticle of various inorganic materials such as iron oxide as well as cobalt oxide, chrome oxide, nickel oxide, uranium oxide, cadmium selenide, and cadmium sulfade. It was confirmed in the following procedures that, just like a recombinant apoferritin, minT1-LF obtained in Example 1 has an ability to form in its interior space a nanoparticle of iron oxide, cobalt oxide, and cadmium selenide.

Figure 5:
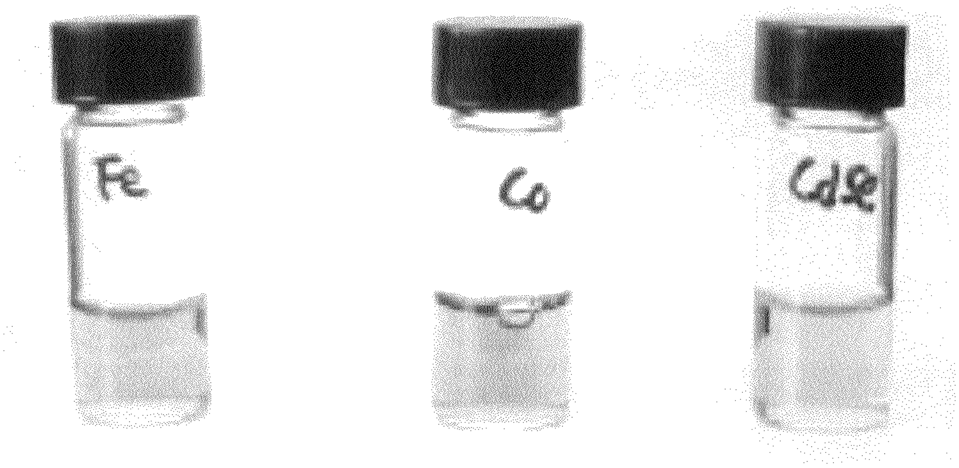
FIG. 5 This figure shows the formations of nanoparticles in the interior space of minT1-LF. The picture shows the appearance of solutions when (from the left) iron-oxide nanoparticles, cobalt-oxide nanoparticles, and cadmium-selenide nanoparticles are formed in the interior space of minT1-LF. The colors of the solutions show that the respective nanoparticles have been formed in the interior space of minT1-LF.

With regard to iron oxide, to a solution comprising 50 mM HEPES-NaOH, pH7.0, and 0.5 mg/ml of minT1-LF, 1/10 volume of Ammonium iron(II) sulfate hexahydrate was added (final concentration 5 mM) and the resultant mixture was allowed to stand still at room temperature overnight (FIG. 5). Subsequently, by a centrifugal operation with an ultracentrifuge (Beckman, TLA 100.4 rotor, 50,000 rpm, 1 hour), minT1-LF was precipitated. This precipitate was dissolved in 50 mM Tris-HCl, pH 8.0, and the procedure of precipitating excessive iron oxide by a centrifugation (Kubota, 5922, RA410M2 rotor, 3000 rpm, 10 minutes) and removing them was repeated twice. The collected minT1-LF was then dialyzed against 50 mM Tris-HCl, pH 8.0. The dialyzed minT1-LF was quantified by BioRad Protein Assay (BioRad), and then used for the following experiments.

With regard to cobalt oxide, to a solution comprising 50 mM HEPES-NaOH, pH 8.3, and 0.3 mg/ml of minT1-LF, cobalt acetate tetrahydrate was added to the final concentration of 3 mM and then hydrogen peroxide was added to the final concentration of 1.5 mM. The resultant mixture was allowed to stand still at 50° C. overnight. Subsequently, by a centrifugal operation with an ultracentrifuge (Beckman, TLA100.4 rotor, 50,000 rpm, 1 hour), minT1-LF was precipitated. This precipitate was dissolved in 50 mM TrisHCl, pH 8.0, and the procedure of precipitating excessive cobalt oxide by a centrifugation (Kubota, 5922, RA410M2 rotor, 3000 rpm, 10 minutes) and removing them was repeated twice. The collected minT1-LF was dialyzed against 50 mM TrisHCl, pH 8.0. The dialyzed minT1-LF was quantified by BioRad Protein Assay (BioRad), and then used for the following experiments.

With regard to cadmium selenide, to a solution comprising 7.5 mM ammonium acetate, 0.5 mg/ml of minT1-LF, and 1 mM cadmium (II) acetate hydrate, selenourea was added to the final concentration of 5 mM and the resultant mixture was allowed to stand still at room temperature overnight. Subsequently, by a centrifugal operation with an ultracentrifuge (Beckman, TLA 100.4 rotor, 50,000 rpm, 1 hour), minT1-LF was precipitated. This precipitate was dissolved in 50 mM TrisHCl, pH 8.0, and the procedure of precipitating excessive cobalt oxide by a centrifugation (Kubota, 5922, RA410M2 rotor, 3000 rpm, 10 minutes) and removing them was repeated twice. The collected minT1-LF was then dialyzed against 50 mM TrisHCl, pH 8.0. The dialyzed minT1-LF was quantified by BioRad Protein Assay (BioRad), and then used for the following experiments.

Figure 6:
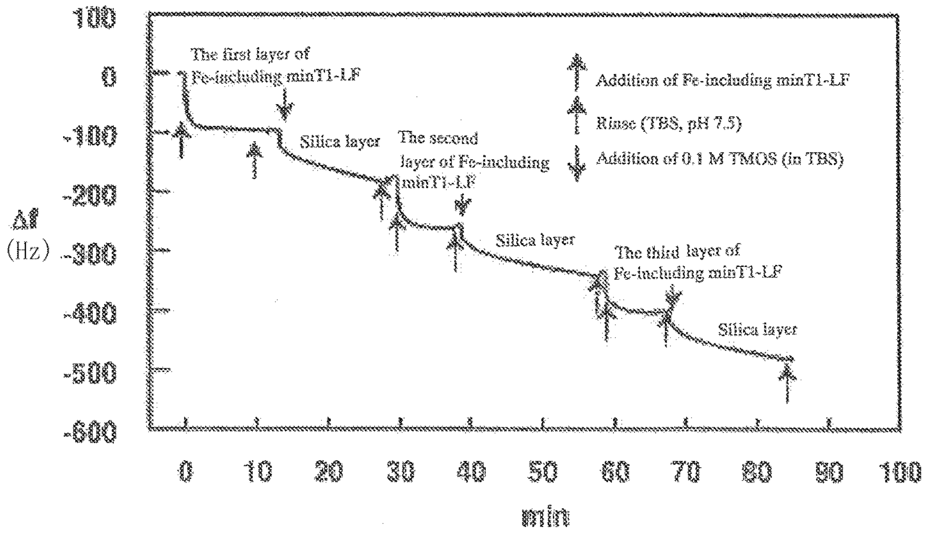
FIG. 6 This figure shows a minT1-LF-mediated control of a three-dimensional positioning of iron-oxide nanoparticles.
Figure 7:
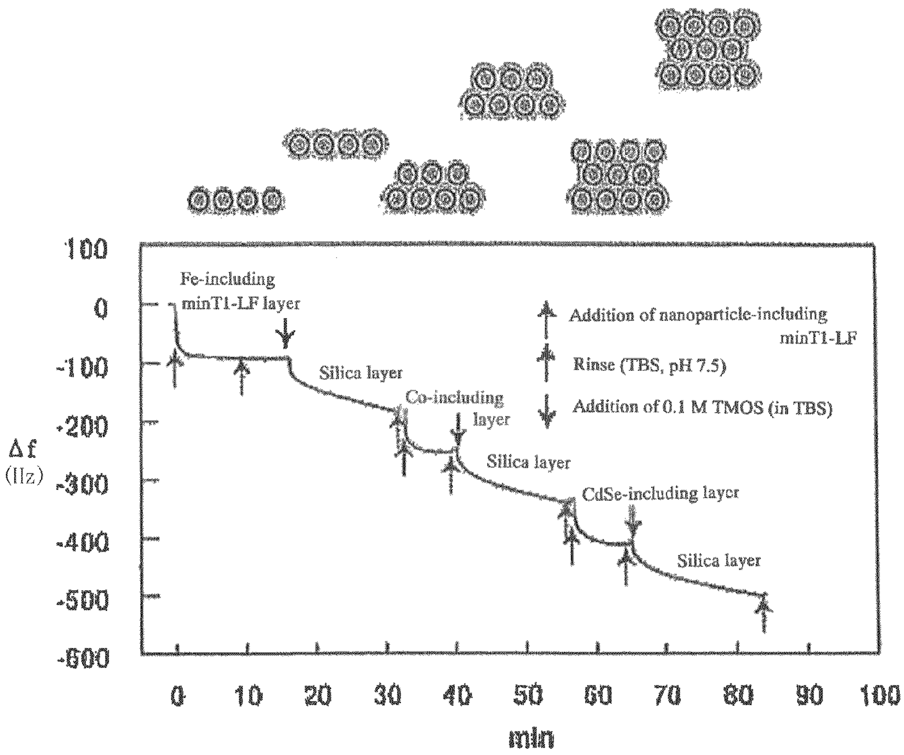
FIG. 7 This figure shows a minT1-LF-mediated control of a three-dimensional positioning of nanoparticles. Sequential layering of minT1-LFs which include iron oxide, cobalt oxide, or cadmium selenide resulted in a successful control of a three-dimensional positioning of different nanoparticles.
Figure 8:
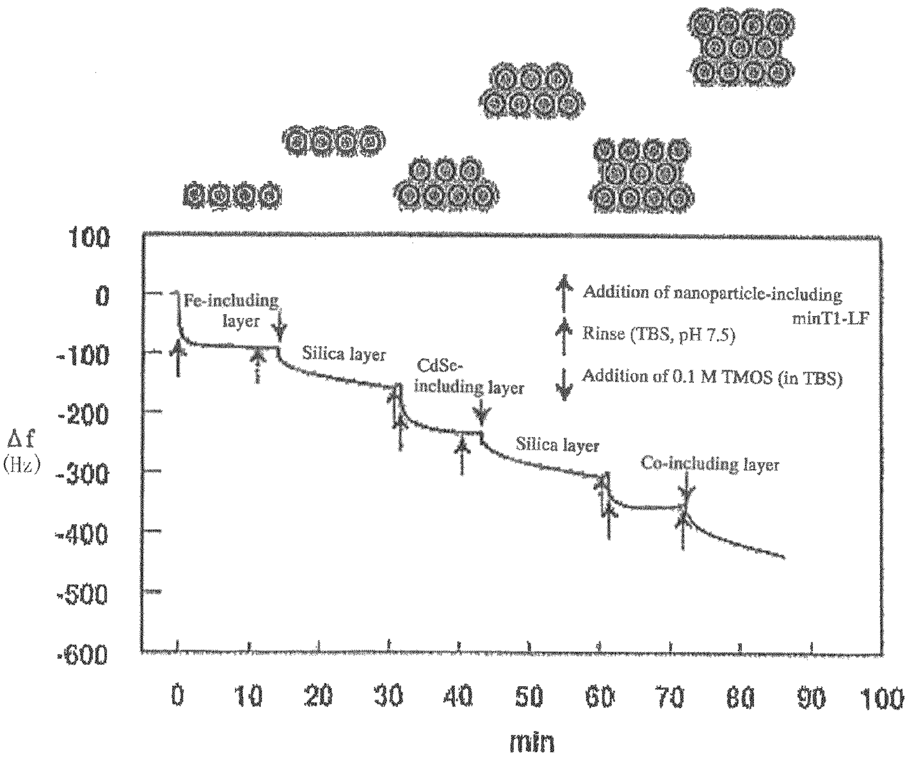
FIG. 8 This figure shows a minT1-LF-mediated control of a three-dimensional positioning of nanoparticles. Sequential layering of minT1-LFs which include iron oxide, cadmium selenide, or cobalt oxide resulted in a successful control of a three-dimensional positioning of different nanoparticles.
Figure 9:
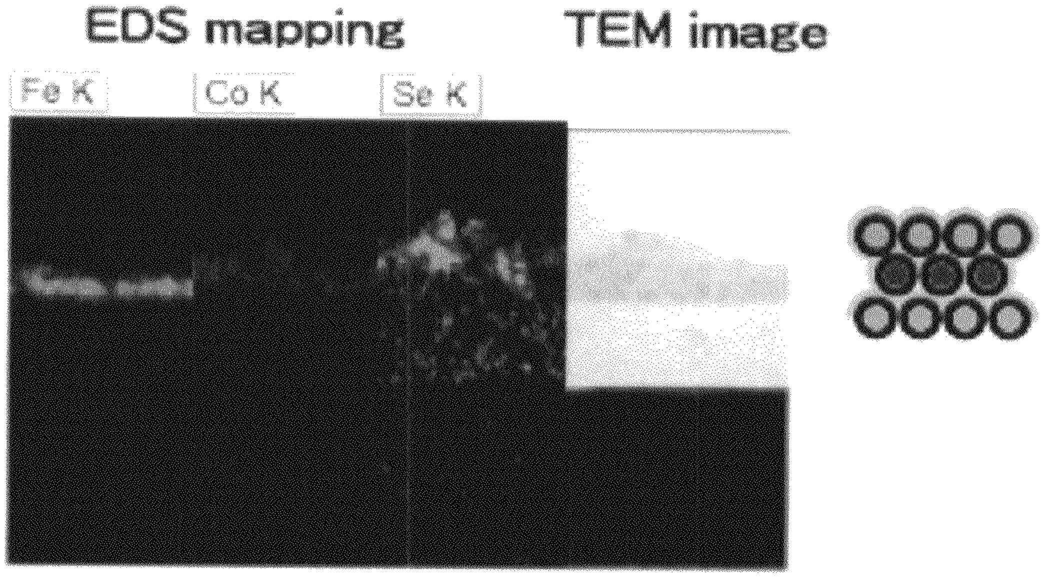
FIG. 9 This figure shows the three-dimensional positioning of nanoparticles (1) aligned via minT1-LF. A transmission electron microscopic image (right) and an elemental mapping (left) of a cross-sectional sample showed that the present method for controlling a three-dimensional positioning functioned effectively.
Figure 10:
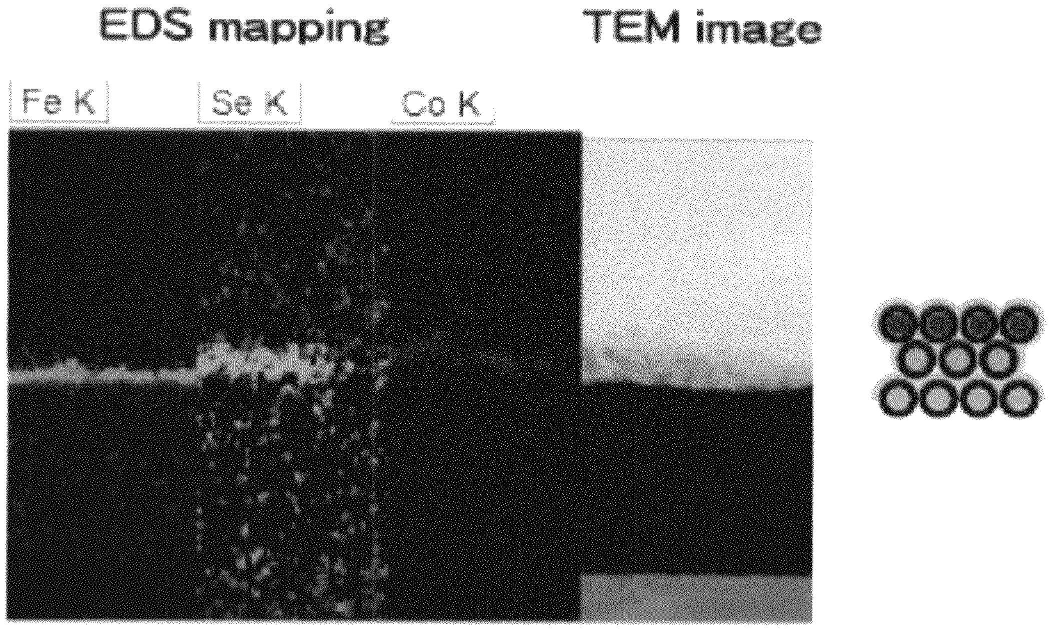
FIG. 10 This figure shows the three-dimensional positioning of nanoparticles (2) aligned via minT1-LF. A transmission electron microscopic image (right) and an elemental mapping (left) of the cross-sectional sample showed that the present method for controlling a three-dimensional positioning functioned effectively.

With the same method as in Example 3, a three-dimensional positioning of nanoparticle-including minT1-LF was performed. The results are shown in FIGS. 6 to 8. It was confirmed that a three-dimensional positioning of minT1-LF was controlled and a thin film of minT1-LF was formed also in the cases where: iron oxide-including minT1-LF (Fe-minT1-LF) was multilayered in three layers (Fe—Fe—Fe) (FIG. 6); the layers were positioned in the order of Fe-minT1-LF, cobalt oxide-including minT1-LF (Co-minT1-LF), and cadmium selenide-including minT1-LF (CdSe-minT1-LF) (Fe—Co—CdSe) (FIG. 7); or the layers were positioned in the order of Fe-minT1-LF, CdSe-minT1-LF, and Co-minT1-LF (Fe—CdSe—Co) (FIG. 8). By an ion thinning method, cross-sectional samples of these multilayered sensors were produced. A transmission electron microscope (TEM, Topcon, EM-002BF/P-20) and an energy dispersive X-ray analyzer (EDS, Thermo, Noran System IV) were used to observe the cross-sectional samples and to confirm the distribution of the metal elements included in minT1-LF (FIGS. 9 and 10). It was successfully confirmed that these samples were multilayered in the same order as they were added in both cases of Fe—Co—CdSe and Fe—CdSe—Co.

The above results confirmed that the method for controlling a three-dimensional positioning and the method for forming a thin film utilizing the multi-functionality of an inorganic material-binding peptide allow a free positioning of plural kinds of functional compounds to intended positions.

Example 5

Assessment Under an Atom Force Microscope

Figure 11:
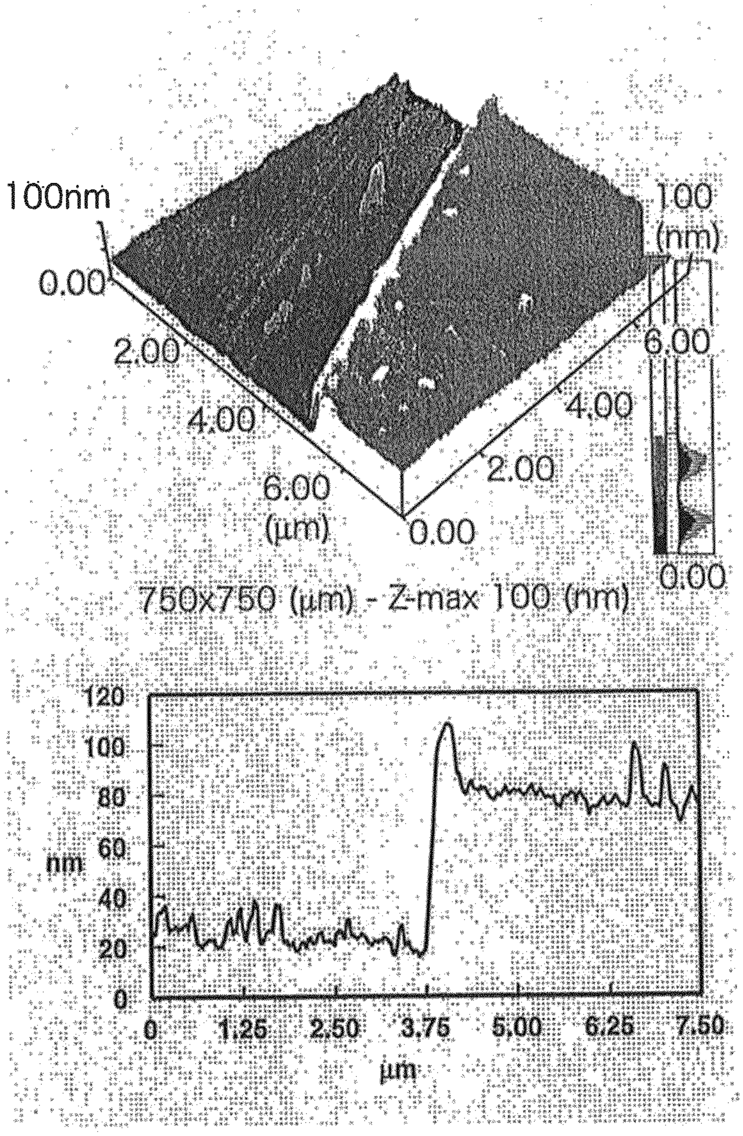
FIG. 11 This figure shows an atomic force microscopic image of a thin film of minT1-LF/silica.

The thin film produced in Example 3 was assessed under an atom force microscope. More specifically, a part of the thin film consisting of minT1-LF/silica layers that were multilayered in three layers on a gold sensor was peeled off by scratching with tweezers and the step was observed under an atom force microscope (SHIMAZU, SPM9500, contact mode) (FIG. 11). The multilayered film was relatively flat and the obtained result regarding the height of the step was not inconsistent with the height conceivable from the molecule size of ferritin.

(Observation Under a Scanning Electron Microscope)

Figure 12:
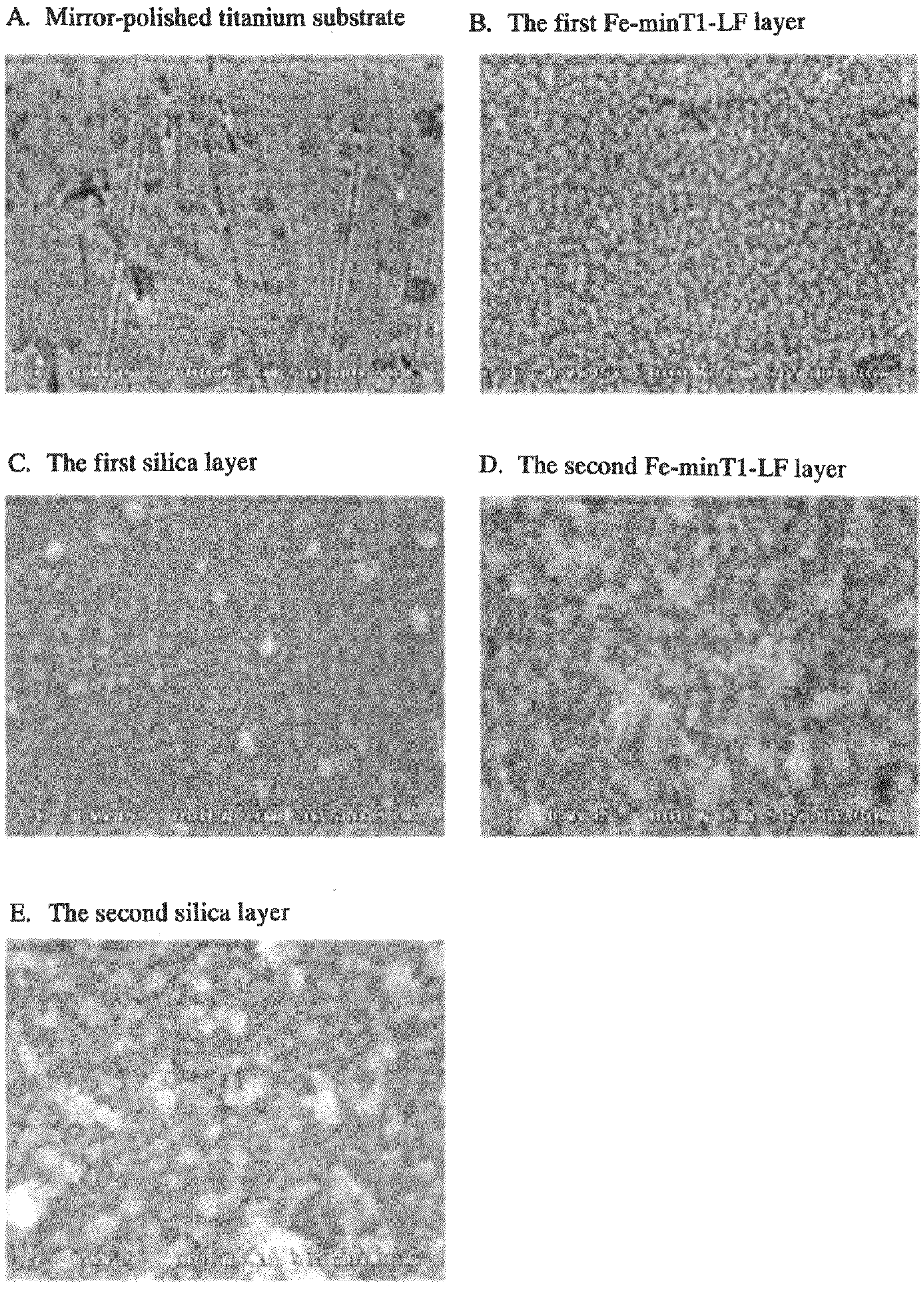
FIG. 12 This set of figures shows electron scanning microscopic images during the process of a controlling of a three-dimensional positioning of Fe-minT1-LF. A: an SEM image of a mirror-polished titanium used as a substrate. Scratches due to polishing are observed; B: an SEM image of when the first layer of Fe-minT1-LF is formed. Granular structures that correspond to minT1-LF are observed; C: an SEM image of when a silica-layer was formed. Not the granular structures that were observed in B but larger structures are observed, which is considered to be due to a silica film formation around minT1-LF; D: an SEM image of when the second layer of Fe-minT1-LF is formed. Again, granular structures that correspond to minT1-LF are observed; E: a further SEM image of when a silica layer is formed. Again, structures generated by the formation of a silica film around minT1-LF are observed.

The processes of Examples 2 to 4 were observed under a scanning electron microscope in the order of events. A type-JIS1 metal titanium, mirror-finished, 6 mm×6 mm (Shinkinzoku Industry Co., Ltd.) was washed well with TBS, then soaked in 0.1 mg/ml of Fe-minT1-LF solution for 10 minutes, then rinsed lightly with TBS, dipped in TBS containing 0.1M TMOS pre-hydrolyzed with 1 mM HCl, and then rinsed lightly again. In addition, by repeating this process, a sample which was multilayered in two layers was produced. The sample from each process was rinsed with ultrapure water, then dried with inactive gas and observed (FIG. 12).

This result and Examples 2 to 4 confirmed that the process of a three-dimensional positioning of minT1-LF using the method for controlling a three-dimensional positioning of the present invention was the same as that is shown schematically in FIG. 1.

Example 7

Manufacture of a Three-Dimensional Structure (a Method for Controlling a Three-Dimensional Positioning or a Method for Producing a Thin-Film)—a Case where the Biomineral Layer is Titanium Dioxide It was shown that, even where the biomineral layer is titanium dioxide, a three-dimensional structure can be formed using the protein model minT1-LF obtained in Example 1. For studying the formation of the structure, QCM-D300 (q-sense AB, Goteborg), a quartz-crystal biomolecule interaction analyzer, was used as a monitor as in Example 2. As a quartz crystal, a gold sensor which was a genuine part for QCM-D300, used in Example 3, was used. The actual measurement temperature was in the neighborhood of 43° C.

Figure 13:
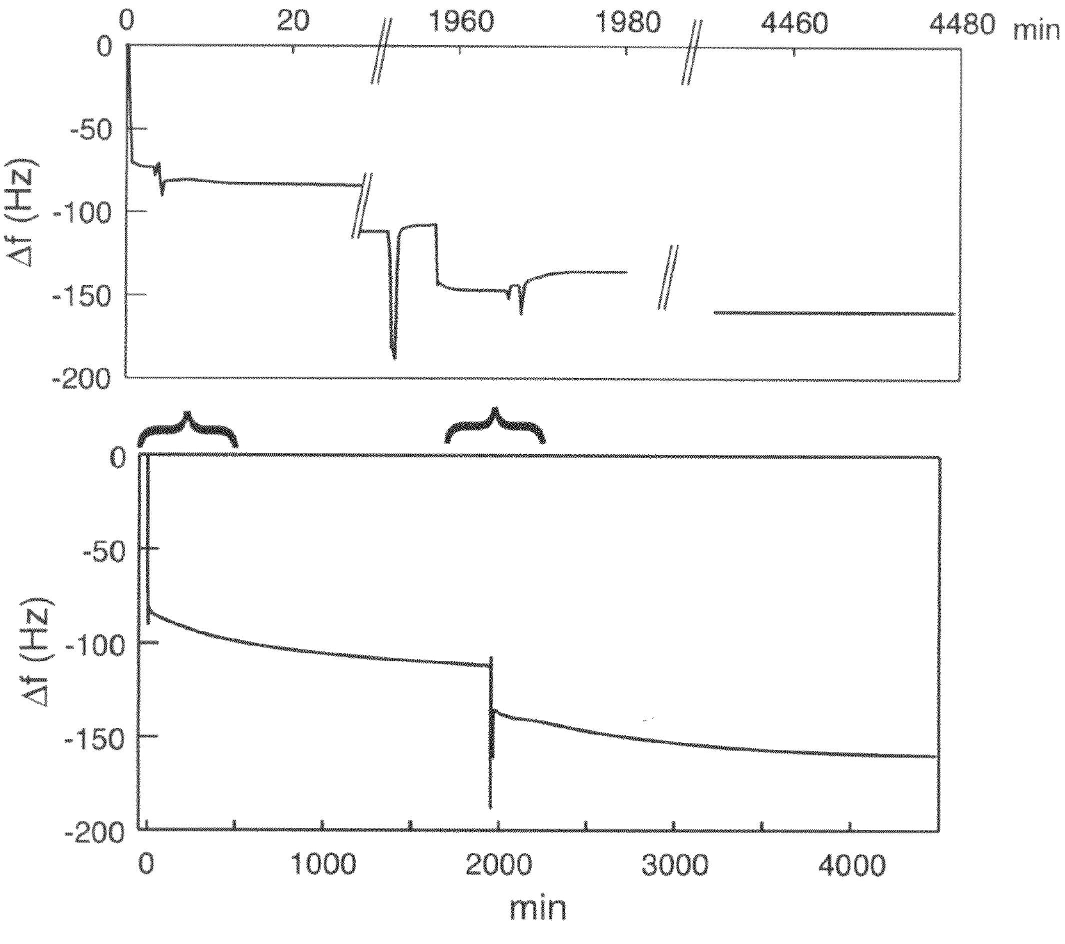
FIG. 13 This set of figures shows a controlling of a three-dimensional positioning via minT1-LF when the biomineral layer is titanium dioxide.

After the reference value was measured a with 50 mM Tris-HCl (pH 7.5) and 150 mM NaCl (TBS), minT1-LF adjusted to the concentration of 0.1 mg/ml was introduced into the measurement chamber and was measured in succession. As shown in FIG. 13, a reduction in frequency was observed in association with the binding of minT1-LF to the gold sensor. After the sensor was stabilized, the inside of the chamber was rinsed with TBS, and TBS added with 1/10 volume of titanium (IV) bis(ammonium lactato) dihydrozide, 50 wt. % solution water (Aldrich) was introduced into the measurement chamber. From the frequency change shown by the QCM-D300, it was possible to monitor the process that titanium dioxide layer was slowly depositing on the minT1-LF film by minT1-LF's ability to biomineralize titanium dioxide. After an about 30-hour incubation, inside of the chamber was rinsed with TBS, and 0.1 mg/ml of minT1-LF was introduced in the measurement chamber. This time, a reduction in frequency was observed in association with the binding of minT1-LF to the titanium dioxide layer due to the titanium dioxide-binding ability of minTBP-1. This means that the second layer of minT1-LF was formed. By repeating the above processes, minT1-LF can be positioned three-dimensionally.

The above results confirmed that the method for controlling a three-dimensional positioning and a method for forming a thin film utilizing the multifunctionality of an inorganic material-binding peptide are effective even where the biomineral layer is titanium dioxide (other than silica).

Example 8

Preparation of a Nanomaterial Such as a Protein Chemically Modified with an Inorganic Material-Binding Peptide (1)

A peptide (KIS-P1: titanium-binding peptide) consisting of the amino acid sequence shown by SEQ ID NO: 47 was bound to wild-type horse spleen-derived type-L ferritin (Dl-LF) used in the control experiment in Example 3, to produce a chemically modified ferritin protein (CM minT1-LF). KIS-P1 is a synthetic peptide wherein, glycine, a flexible linker; triptophan, an ultraviolet absorption marker; and cysteine having on its side chain a thiol group to be targeted by a cross-linking agent, are sequentially added at the carboxyl-end side of the titanium-binding peptide RKLPDA (minTBP-1). More specifically, CM minT1-LF was produced according to the following procedures. In brief, 10 mM N-succinimidyl iodoacetate (SIA) dissolved in 25 μl of DMSO was added to 5 mg/ml of DL-LF in 1 ml of PBS solution; the resultant mixture was stirred at room temperature for 1 hour and then dialyzed against a PBS solution; and after the removal of unreacted SIA, the synthetic peptide shown by SEQ ID NO: 47 was added so that the final concentration becomes 1 mM. Ferritin was chemically modified with the peptide shown by SEQ ID NO: 47 by stirring the mixture at room temperature for 3 hours, and then dialyzed again to remove the unreacted synthetic peptide shown by SEQ ID NO: 47.

The CM minT1-LF thus produced was diluted 25-fold and used to show that a three-dimensional structure can be formed. For studying the formation of the structure, QCM-D300 (q-sense AB, Goteborg), a quartz-crystal biomolecule interaction analyzer, was used as a monitor as in Example 2. As a quartz crystal, a titanium sensor which was a genuine part for QCM-D300, used in Example 2, was used. The actual measurement temperature was about 24.8° C.

Figure 14:
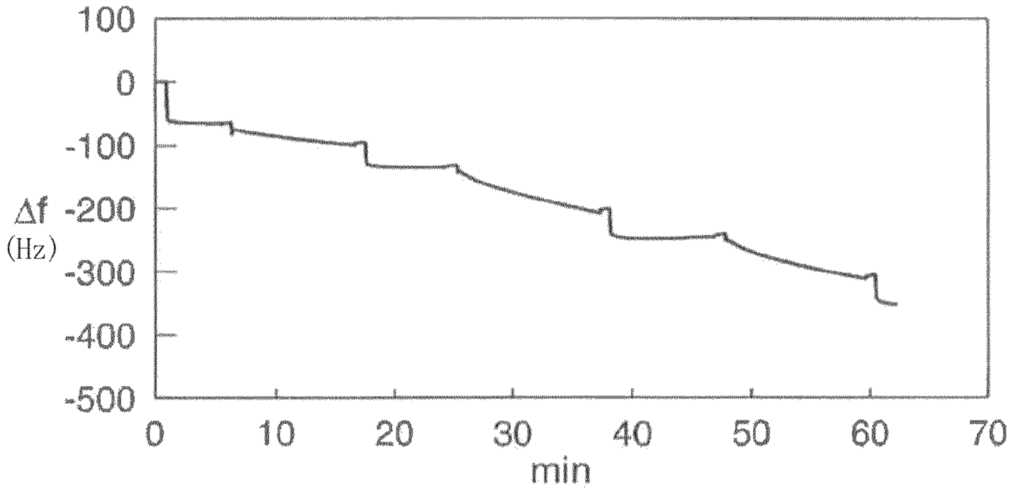
FIG. 14 This figure shows a controlling of a three-dimensional positioning by ferritin proteins that are chemically modified with a synthetic peptide comprising a titanium-binding peptide (KIS-P1) sequence.

After the reference value was measured with PBS, the diluted CM minT1-LF was introduced into the measurement chamber and was measured in succession. As shown in FIG. 14, a reduction in frequency was observed in association with the binding of CM minT1-LF to the titanium sensor. After the sensor was stabilized, the inside of the chamber was rinsed with PBS, and PBS added with 1/10 volume of 1M tetramethoxysilane (TMOS) pre-hydrolyzed with 1 mM hydrochloric acid was introduced into the measurement chamber. From the frequency change shown by the QCM-D300, it is possible to monitor the process that a silica layer is slowly depositing on the CM minT1-LF film by CM minT1-LF's ability to biomineralize silica. After a brief incubation, inside of the measurement chamber was rinsed with PBS, and 0.1 mg/ml of CM minT1-LF was introduced into the measurement chamber. This time, a reduction in frequency was observed in association with the binding of CM minT1-LF to the silica layer due to the silica-binding ability of CM minT1-LF. This means that the second layer of CM minT1-LF was formed. By repeating the above processes, CM minT1-LF was successfully positioned three-dimensionally.

Example 9

Preparation of a Nanomaterial Such as a Protein Chemically Modified with an Inorganic Material-Binding Peptide-2

Next, it will be shown that proteins other than ferritin can be used in the same manner to produce an aggregate presenting on its surface inorganic material-binding peptides, by chemically modifying such proteins with chemically synthesized inorganic material-binding peptides. The protein used was a firefly-derived luciferase (Aldrich). A luciferase protein which was chemically modified with a synthetic peptide consisting of the amino acid sequence shown by SEQ ID NO: 47 (CM-luc) was produced according to the following procedures. 10 mM N-succinimidyl iodoacetate (SIA) dissolved in 8 μl of DMSO was added to 2 mg/ml of luciferase protein in 0.2 ml of PBS solution. The resultant mixture was stirred at room temperature for 1.5 hours and then dialyzed against a PBS solution to remove unreacted SIA. Subsequently, synthetic peptides shown by SEQ ID NO: 47 were added so that the final concentration becomes 1 mM. The resultant mixture was stirred at room temperature for 6 hours to chemically modify luciferase protein with the synthetic peptide shown by SEQ ID NO: 47, and then dialyzed again to remove the unreacted synthetic peptide shown by SEQ ID NO: 47.

The CM-luc thus produced, which was chemically modified with the synthetic peptide shown by SEQ ID NO: 47, was diluted 20-fold with PBS, and then used to show that a three-dimensional structure can be formed. For studying the formation of the structure, QCM-D300 (q-sense AB, Goteborg), a quartz-crystal biomolecule-interaction analyzer, was used as a monitor as in Example 2. As a quartz crystal, a titanium sensor which was a genuine part for QCM-D300, used in Example 2, was used. The actual measurement temperature was about 24.8° C.

Figure 15:
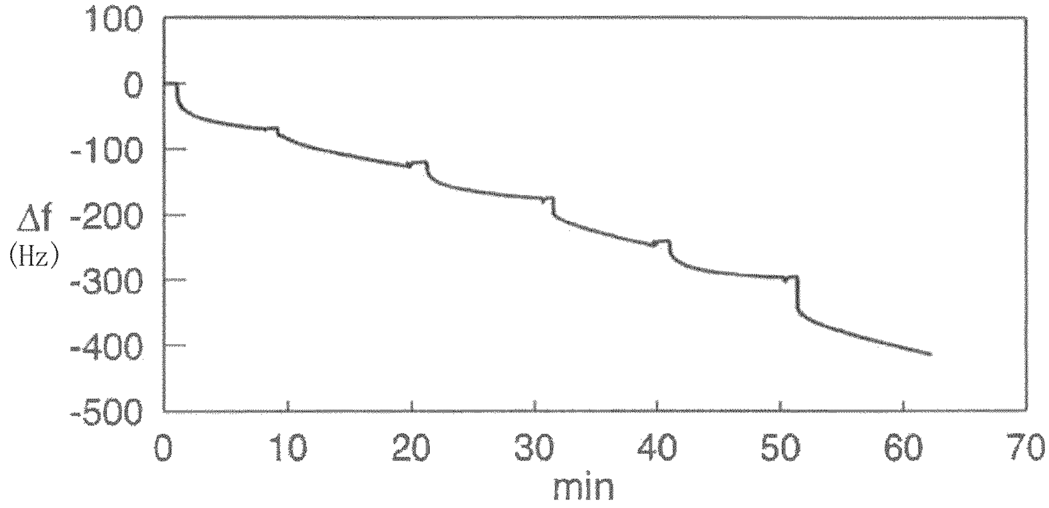
FIG. 15 This figure shows a controlling of a three-dimensional positioning when luciferase was added to a nanomaterial such as a protein that was chemically modified with an inorganic material-binding peptide.

After the reference value was measured with PBS, the diluted CM minT1-LF was introduced into the measurement chamber and was measured in succession. As shown in FIG. 15, a reduction in frequency was observed in association with the binding of CM-luc to the titanium sensor. After the sensor was stabilized, the inside of the chamber was rinsed with PBS, and PBS added with 1/10 volume of 1 mM tetramethoxysilane (TMOS) pre-hydrolyzed with 1 mM hydrochloric acid was introduced into the measurement chamber. From the frequency change shown by the QCM-D300, it is possible to monitor the process that a silica layer is slowly depositing on the CM-luc film by CM-luc's ability to biomineralize silica. After a brief incubation, inside of the chamber was rinsed with PBS, and 0.1 mg/ml of CM-luc was further introduced in the measurement chamber. This time, the reduction in frequency was observed in association with the binding of CM-luc to the silica layer due to the silica-binding ability of CM-luc. This means that the second layer of CM-luc was formed. By repeating the above processes, CM-luc was successfully positioned three-dimensionally.

Example 10

Preparation of a Nanomaterial Such as a Synthetic Polymer Chemically Modified with an Inorganic Material-Binding Peptide Next, it will be shown that synthetic high molecular materials other than proteins can be used to produce an aggregate which is presenting on its surface inorganic material-binding peptides, by chemically modifying with chemically synthesized inorganic material-binding peptides. The synthetic high molecule used was Acetal-PEG/PAMA, which is a block copolymer (Langmuir 20 p 561, 2004). A block copolymer chemically modified with synthetic peptides consisting of the amino acid sequence shown by SEQ ID NO: 47 (minTBP-1-PEG/PAMA) were produced according to the following procedures. 250 mg Acetal-PEG/PAMA was dissolved with 5 ml of 90% acetic acid. The resultant mixture was stirred at 35° C. for 5 hours, and dialyzed against 0.1 M sodium acetate buffer solution, pH5.5. Then, 27.7 mg of N-(β-maleimidopropionic acid) hydrazide (BMPH) dissolved in DMSO was added and the resultant mixture was stirred at room temperature for 2 hours. Again, the mixture was dialyzed against 0.1 M sodium acetate buffer solution, pH 5.5, to remove the unreacted BMPH, then the solvent of dialysis was substituted for water, and the dialyzed substance was lyophilized. 100 mg of such PEG/PAMA(Mal-PEG/PAMA) whose terminal end is converted from Acetal to maleimide and 24 mg of the systhetic peptide shown by SEQ ID NO: 47 was dissolved in 20 ml of 50 mM Tris-hydrochloric buffer solution, pH 7.5, and the resultant mixture was stirred at room temperature overnight to chemically modify PEG/PAMA with the synthetic peptide shown by SEQ ID NO: 47. The resultant substance was dialyzed against water to remove the unreacted synthetic peptide shown by SEQ ID NO: 47, and then lyophilized.

Figure 16:
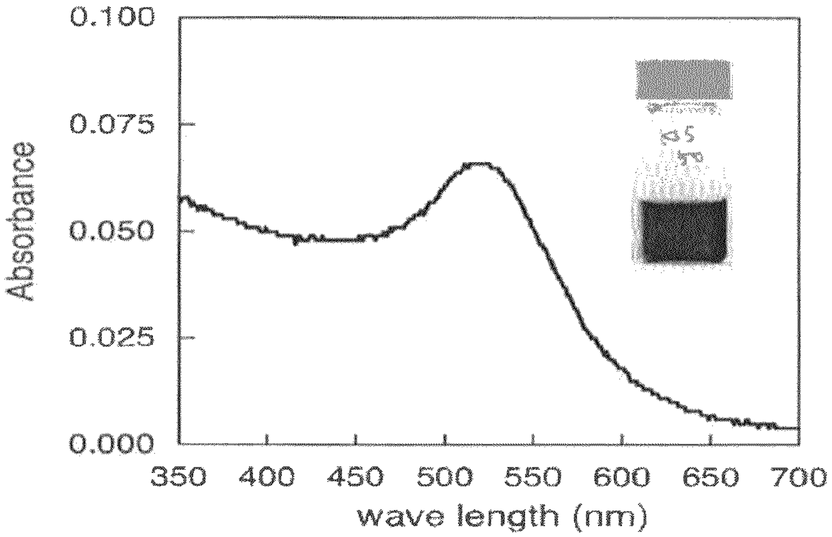
FIG. 16 This figure shows a formation of nanoparticles in the interior space of minTBP-1-PEG/PAMA. The upper right picture shows the appearance of the solution when minTBP-1-PEG/PAMA-gold nanoparticle was formed in the interior space of minTBP-1-PEG/PAMA. The color of the solution shows that the respective nanoparticles have been formed in the interior space of minTBP-1-PEG/PAMA. The purified product showed an absorbance profile with the maximum absorption in the neighborhood of 520 nm showing the formation of gold nanoparticles, which shows that the respective nanoparticles were formed in the interior space of minTBP-1-PEG/PAPA.
Figure 17:
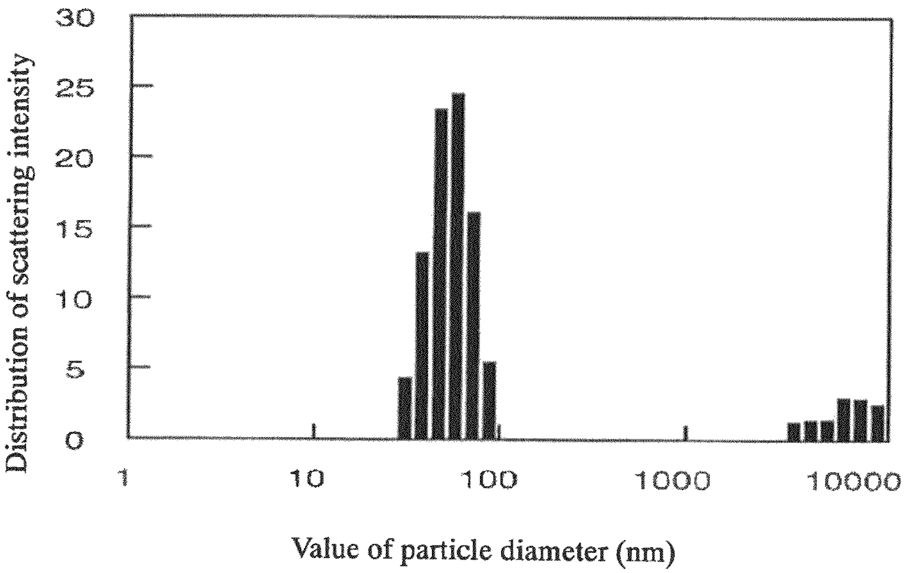
FIG. 17 This figure shows measurement results of a dynamic light scattering of minTBP-1-PEG/PAMA. The mean particle diameter of core-shell structures of minTBP-1-PEG/PAPA-gold nanoparticle is expected to be 54.5 nm.

It is shown in the following procedures that minTBP-1-PEG/PAMA thus produced, as with the case reported in Langmuir 20 p 561, 2004, keeps an ability to form a micelle including gold nanoparticles from a chloroauric acid solution. 10 mg of minTBP-1-PEG/PAMA was dissolved with 2 ml of PBS. Then, this mixture was added with 50 μL of 40 mg/ml of chloroauric acid tetrahydrate ($HAuC14.4H_2O$) dissolved also in PBS. The resultant mixture was stirred at room temperature overnight. Consequently, the reaction liquid displayed a red color, which showed that gold nanoparticles were formed (FIG. 16). The procedure of precipitating this product by an ultracentrifugation, TLA, 100.4 rotor, 30,000 rpm, 30 minutes, removing the supernatant, and then stirring in PBS was repeated three times to purify a gold nanoparticle and a block copolymer forming a core-shell structure. An absorbance measurement of the purified product also provided a profile having the maximum absorbance in the neighborhood of 520 nm, which showed the formation of a gold nanoparticle (FIG. 16). Further, the dynamic light scattering was measured and it was estimated that the mean particle diameter of the core-shell structures of minTBP-1-PEG/PAMA-gold nanoparticle was 54.5 nm (FIG. 17). The above showed that it is possible to provide the synthetic peptide shown by SEQ ID NO: 47 to PEG/PAMA by a chemical modification without losing the characteristics of PEG/PAMA.

The results of Examples 8, 9, and 10 confirmed that it is possible to provide inorganic material-binding peptides to nanomaterials such as proteins and synthetic high molecules by chemically modifying the above nanomaterials with a chemically synthesized inorganic material-binding peptide. It was also confirmed that the method for controlling a three-dimensional positioning and the method for forming a thin film, by a function of an inorganic material-binding peptide added by a chemical modification, are effective.

INDUSTRIAL APPLICABILITY

The present invention is a technique which enables a three-dimensional positioning of an inorganic material on a thin film and of an inorganic nanoparticle supported on an aggregate at the nanoscale, by utilizing the fact that a peptide having a binding ability to an inorganic material is a multi-functional peptide having two qualities: (1) that, in addition to a binding ability, the peptide has an ability to promote the mineralization of molecules constituting a target inorganic substance, and; (2) that the peptide has a binding ability to a plurality of, but to a limited range of, inorganic materials. For example, peptide motif TBP-1 consisting of 12 amino acid residues (SEQ ID NO: 2), having an ability to bind to titanium, is capable of binding to the surface of silver and silica other than titanium, but does not bind to the surface of other metals such as gold, platinum, chromium, iron, copper, tin, or zinc. In addition, TBP-1 peptide can promote the mineralization reaction of titanium dioxide, silver, and silicon in vitro. Such multifuctionality of TBP-1 is maintained even when this peptide is fused with other proteins. More specifically, fusing the nucleotide sequence encoding minTPB-1 sequence (SEQ ID NO: 1), the core sequence of TBP-1, to the 5' terminal of the subunit gene of a ferritin protein provides a modified subunit of ferritin-protein. From this modified subunit, a modified ferritin protein can be synthesized, which presents on its surface 24 molecules of minTBP-1. This minTBP-1-presenting ferritin protein binds strongly to the surface of titanium, slica, or silver, but does not bind to the surface of gold. In addition, this minTBP-1-presenting ferritin protein keeps the ability to promote the biomineralization of titanium dioxide, silica, and silver in vitro.

For example, when the above minTBP-1-presenting ferritin proteins are developed on a titanium substrate, the proteins form a monolayer on the titanium substrate due to their titanium-binding ability. Since the binding of minTBP-1-presenting ferritin protein and the titanium substrate does not use all of the 24 minTBP-1s, minTBP-1s that were not used in the binding can exert the mineralization activity. Indeed, when tetramethoxysilane (TMOS), a silica precursor, is added to minTBP-1-presenting ferritin proteins that have formed a monolayer on a titanium substrate, a biomineral layer of silica can be further layered on the monolayer of minTBP-1-presenting ferritin proteins. Next, to this biomineral layer, the second layer of minTBP-1-presenting ferritin proteins can be layered by utilizing the binding ability of minTBP-1 to silica. By repeating this operation, the production of a thin film of ferritin protein, wherein the thickness is controlled at the nanoscale can be realized.

Since functional nanocompounds such as semiconductor nanoparticles can be included in ferritin molecules, by using ferritin particles including different functional nanocompounds, a multilayered structure of plural kinds of functional nanocompounds can be produced accurately at the nanoscale, and this has a high utility value in the areas of semiconductor and nanobiotechnology.

Further, examples of the subjects of the controlling of a three-dimensional positioning and the formation of thin film include protein, virus, phage, block copolymer, and high molecule; and a quantum dot, semiconductor material, condensing element, fluorescent molecule and the like that is added thereto by an inclusion, conjugation, chemical modification, or adsorption.

The invention claimed is:

1. A multilayered three-dimensional structure comprising in the order of:

(a) an inorganic substrate, (b) an aggregate comprising and presenting on its surface a plurality of inorganic material-binding peptides consisting of the amino acid sequence shown in SEQ ID NO: 1, said aggregate of peptides (b) bound as a monolayer onto said inorganic substrate (a), and (c) a biomineral layer formed from a substrate for a biomineralization reaction or a precursor for a biomineralization reaction by a biomineralization ability of the inorganic material-binding peptides, on the side of said aggregate of peptides (b), which is not bound to said inorganic substrate (a), wherein the inorganic substrate (a) comprises at least one selected from the group consisting of titanium, silicon, silver, and gold, and wherein the biomineral layer (c) is formed from at least one selected from the group consisting of silicon, silver, titanium, silicon oxides, silver oxides, and titanium oxides.

2. The multilayered three-dimensional structure according to claim 1, further comprising in the order of:

(d) a further aggregate comprising and presenting on its surface a further plurality of inorganic material-binding peptides consisting of the amino acid sequence shown in SEQ ID NO: 1 and supporting an inorganic nanoparticle, said further aggregate of peptides (d) bound to the biomineral layer (c) on the side not bound to said aggregate of peptides (b), and (e) a further biomineral layer formed on the unbound side of (d) from a substrate for a biomineralization reaction or a precursor for a biomineralization reaction by a biomineralization ability of the further inorganic material-binding peptides supporting the bound inorganic nanoparticle; and optionally further comprising additional further layers of aggregate of peptides, supporting bound inorganic nanoparticle, and biomineral layer, in the order thereof, wherein the biomineral layer (e) is formed from at least one selected from the group consisting of silicon, silver, titanium, silicon oxides, silver oxides, and titanium oxides.

3. The multilayered three-dimensional structure according to claim 1, further comprising in the order of:

(f) a further aggregate comprising and presenting on its surface a further plurality of inorganic material-binding peptides consisting of the amino acid sequence shown in SEQ ID NO: 1, said further aggregate of peptides (f) bound to the biomineral layer (c) on the side not bound to said aggregate of peptides (b), and (g) a further biomineral layer formed on the unbound side of (f) from a substrate for a biomineralization reaction or a precursor for a biomineralization reaction by a biomineralization ability of the further inorganic material-binding peptides; and optionally further comprising additional further layers of aggregate of peptides and biomineral layer, in the order thereof, wherein the biomineral layer (g) is formed from at least one selected from the group consisting of silicon, silver, titanium, silicon oxides, silver oxides, and titanium oxides.

* * * * *

SEQUENCE LISTING

<160> NUMBER OF SEQ ID NOS: 48

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
peptide having binding ability:Ti

<400> SEQUENCE: 1

Arg Lys Leu Pro Asp Ala
1 5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:Ti

<400> SEQUENCE: 2

Arg Lys Leu Pro Asp Ala Pro Gly Met His Thr Trp
1 5 10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
peptide having binding ability:Ti

<400> SEQUENCE: 3

Arg Ala Leu Pro Asp Ala
1 5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:nano carbon

<400> SEQUENCE: 4

Asp Tyr Phe Ser Ser Pro Tyr Tyr Glu Gln Leu Phe
1 5 10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide having binding ability:nano carbon

<400> SEQUENCE: 5

Tyr Asp Pro Phe His Ile Ile
1 5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic -continued peptide having binding ability:GaAs

<400> SEQUENCE: 6

Ala Gln Asn Pro Ser Asp Asn Asn Thr His Thr His
1 5 10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:GaAs

<400> SEQUENCE: 7

Arg Leu Glu Leu Ala Ile Pro Leu Gln Gly Ser Gly
1 5 10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:GaAs

<400> SEQUENCE: 8

Thr Pro Pro Arg Pro Ile Gln Tyr Asn His Thr Ser
1 5 10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:CaCO3

<400> SEQUENCE: 9

His Thr Gln Asn Met Arg Met Tyr Glu Pro Trp Phe
1 5 10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:CaCO3

<400> SEQUENCE: 10

Asp Val Phe Ser Ser Phe Asn Leu Lys His Met Arg
1 5 10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
peptide having binding ability:Ag

<400> SEQUENCE: 11

Ala Tyr Ser Ser Gly Ala Pro Pro Met Pro Pro Phe
1 5 10

<210> SEQ ID NO 12

<211> LENGTH: 12
<212> TYPE: PRT
<213> ORGANISM: Artificial Sequence
<220> FEATURE:
<223> OTHER INFORMATION: Description of Artificial Sequence: Synthetic peptide having binding ability:Ag

<400> SEQUENCE: 12

Asn Pro Ser Ser Leu Phe Arg Tyr Leu Pro Ser Asp
1 5 10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic peptide having binding ability:Ag

<400> SEQUENCE: 13

Ser Leu Ala Thr Gln Pro Pro Arg Thr Pro Pro Val
1 5 10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic peptide having binding ability:SiO2

<400> SEQUENCE: 14

Met Ser Pro His Pro His Pro Arg His His His Thr
1 5 10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic peptide having binding ability:SiO2

<400> SEQUENCE: 15

Arg Gly Arg Arg Arg Arg Leu Ser Cys Arg Leu Leu
1 5 10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic peptide having binding ability:SiO2

<400> SEQUENCE: 16

Lys Pro Ser His His His His His Thr Gly Ala Asn
1 5 10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide having binding ability:ZnS

<400> SEQUENCE: 17

Cys Asn Asn Pro Met His Gln Asn Cys
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:Pt

<400> SEQUENCE: 18

Cys Asp Arg Thr Ser Thr Trp Arg Cys
1 5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:Pt

<400> SEQUENCE: 19

Cys Gln Ser Val Arg Ser Thr Lys Cys
1 5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:Pt

<400> SEQUENCE: 20

Cys Ser Ser Ser His Leu Asn Lys Cys
1 5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:Pd

<400> SEQUENCE: 21

Cys Ser Val Thr Gln Asn Lys Tyr Cys
1 5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:Pd

<400> SEQUENCE: 22

Cys Ser Pro His Pro Gly Pro Tyr Cys
1 5

<210> SEQ ID NO 23
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide having binding ability:Pd

<400> SEQUENCE: 23

Cys His Ala Pro Thr Pro Met Leu Cys
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide having binding ability:Fe2O3

<400> SEQUENCE: 24

Arg Arg Thr Val Lys His His Val Asn
1               5

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide having binding ability:Au

<400> SEQUENCE: 25

Met His Gly Lys Thr Gln Ala Thr Ser Gly Thr Ile Gln Ser
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide having binding ability:Au

<400> SEQUENCE: 26

Leu Gly Gln Ser Gly Gln Ser Leu Gln Gly Ser Glu Lys Thr Asn Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide having binding ability:Au

<400> SEQUENCE: 27

Glu Lys Leu Val Arg Gly Met Glu Gly Ala Ser Leu His Pro Ala
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide having binding ability:Cr2O3

<400> SEQUENCE: 28

Val Val Arg Pro Lys Ala Ala Thr Asn
1               5

-continued

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:Cr2O3

<400> SEQUENCE: 29

Arg Ile Arg His Arg Leu Val Gly Gln
1 5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
peptide having binding ability:PbO2

<400> SEQUENCE: 30

Tyr Pro Pro Phe His Asn Asn Asp His Arg Ser
1 5 10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
peptide having binding ability:PbO2

<400> SEQUENCE: 31

Ser Lys Pro Leu Ala Arg Ser Ser Gly Ala
1 5 10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:PbO2

<400> SEQUENCE: 32

Gly Arg Met Gln Arg Arg Val Ala His
1 5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
peptide having binding ability:PbO2

<400> SEQUENCE: 33

Leu Gly Lys Asp Arg Pro His Phe His Arg Ser
1 5 10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
peptide having binding ability:MnO2

<400> SEQUENCE: 34

-continued

His His Met Leu Arg Arg Arg Asn Thr
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic peptide having binding ability:MnO2

<400> SEQUENCE: 35

His Ile Asn Ala Ser Gln Arg Val Ala
1 5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide having binding ability:ZnO

<400> SEQUENCE: 36

Thr Arg Arg Gly Thr His Asn Lys Asp
1 5

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic peptide having binding ability:ZnO

<400> SEQUENCE: 37

Asn Thr Arg Met Thr Ala Arg Gln His Arg Ser Ala Asn His Lys Ser
1 5 10 15

Thr Gln Arg Ala Arg Ser
20

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic peptide having binding ability:Zeolites

<400> SEQUENCE: 38

Met Asp His Gly Lys Tyr Arg Gln Lys Gln Ala Thr Pro Gly
1 5 10

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic peptide having binding ability:Zeolites

<400> SEQUENCE: 39

Val Lys Thr Gln Ala Thr Ser Arg Glu Glu Pro Pro Arg Leu Pro Ser
1 5 10 15

Lys His Arg Pro Gly
20

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
DMP-1peptide:pA

<400> SEQUENCE: 40

```
Glu Ser Gln Glu Ser
1               5
```

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
DMP-1peptide:pB

<400> SEQUENCE: 41

```
Gln Glu Ser Gln Ser Glu Gln Asp Ser
1               5
```

<210> SEQ ID NO 42
<211> LENGTH: 174
<212> TYPE: PRT
<213> ORGANISM: Equus caballus

<400> SEQUENCE: 42

```
Ser Ser Gln Ile Arg Gln Asn Tyr Ser Thr Glu Val Glu Ala Ala Val
1               5                   10                  15

Asn Arg Leu Val Asn Leu Tyr Leu Arg Ala Ser Tyr Thr Tyr Leu Ser
            20                  25                  30

Leu Gly Phe Tyr Phe Asp Arg Asp Asp Val Ala Leu Glu Gly Val Cys
        35                  40                  45

His Phe Phe Arg Glu Leu Ala Glu Glu Lys Arg Glu Gly Ala Glu Arg
    50                  55                  60

Leu Leu Lys Met Gln Asn Gln Arg Gly Gly Arg Ala Leu Phe Gln Asp
65                  70                  75                  80

Leu Gln Lys Pro Ser Gln Asp Glu Trp Gly Thr Thr Pro Asp Ala Met
                85                  90                  95

Lys Ala Ala Ile Val Leu Glu Lys Ser Leu Asn Gln Ala Leu Leu Asp
            100                 105                 110

Leu His Ala Leu Gly Lys Ala Gln Ala Asp Pro His Leu Cys Asp Phe
        115                 120                 125

Leu Glu Ser His Phe Leu Asp Glu Glu Val Lys Leu Ile Lys Lys Met
    130                 135                 140

Gly Asp His Leu Thr Asn Ile Gln Arg Leu Val Gly Ser Gln Ala Gly
145                 150                 155                 160

Leu Gly Glu Tyr Leu Phe Glu Arg Leu Thr Leu Lys His Asp
                165                 170
```

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
linker:BamHI

<400> SEQUENCE: 43

Gly Ala Thr Cys Cys Ala Thr Gly Cys Gly Cys Ala Ala Ala Cys Thr
1 5 10 15

Thr Cys Cys Gly Gly Ala Thr Gly Cys Gly Ala Gly Cys Thr
20 25 30

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic linker:Sal I

<400> SEQUENCE: 44

Cys Gly Cys Ala Thr Cys Cys Gly Gly Ala Ala Gly Thr Thr Thr Gly
1 5 10 15

Cys Gly Cys Ala Thr Gly
20

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic primer:BamHI

<400> SEQUENCE: 45

Gly Thr Gly Gly Ala Ala Thr Thr Gly Thr Gly Ala Gly Cys Gly
1 5 10 15

<210> SEQ ID NO 46
<211> LENGTH: 181
<212> TYPE: PRT
<213> ORGANISM: Artificial Sequence
<220> FEATURE:
<223> OTHER INFORMATION: Description of Artificial Sequence: Synthetic minT1-LF polypeptide

<400> SEQUENCE: 46

Met Arg Lys Leu Pro Asp Ala Ser Ser Gln Ile Arg Gln Asn Tyr Ser
1 5 10 15

Thr Glu Val Glu Ala Ala Val Asn Arg Leu Val Asn Leu Tyr Leu Arg
20 25 30

Ala Ser Tyr Thr Tyr Leu Ser Leu Gly Phe Tyr Phe Asp Arg Asp Asp
35 40 45

Val Ala Leu Glu Gly Val Cys His Phe Phe Arg Glu Leu Ala Glu Glu
50 55 60

Lys Arg Glu Gly Ala Glu Arg Leu Leu Lys Met Gln Asn Gln Arg Gly
65 70 75 80

Gly Arg Ala Leu Phe Gln Asp Leu Gln Lys Pro Ser Gln Asp Glu Trp
85 90 95

Gly Thr Thr Pro Asp Ala Met Lys Ala Ala Ile Val Leu Glu Lys Ser
100 105 110

Leu Asn Gln Ala Leu Leu Asp Leu His Ala Leu Gly Ser Ala Gln Ala
115 120 125

Asp Pro His Leu Cys Asp Phe Leu Glu Ser His Phe Leu Asp Glu Glu
130 135 140

Val Lys Leu Ile Lys Lys Met Gly Asp His Leu Thr Asn Ile Gln Arg
145 150 155 160

-continued

```
Leu Val Gly Ser Gln Ala Gly Leu Gly Glu Tyr Leu Phe Glu Arg Leu
                165                 170                 175

Thr Leu Lys His Asp
            180


<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      KIS-P1 peptide

<400> SEQUENCE: 47

Arg Lys Leu Pro Asp Ala Gly Trp Cys
1               5


<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      Partial peptide R5

<400> SEQUENCE: 48

Ser Ser Lys Lys Ser Gly Ser Tyr Ser Gly Ser Lys Gly Ser Lys Arg
1               5                   10                  15

Arg Ile Leu
```